US005306639A

United States Patent [19]

Matsushiro

[11] Patent Number: 5,306,639

[45] Date of Patent: Apr. 26, 1994

[54] DNA ENCODING GLUCANASE ENZYMES

[76] Inventor: Aizo Matsushiro, 4-15-2, Suite 565, Aoyamadai, Japan

[21] Appl. No.: 772,850

[22] Filed: Oct. 8, 1991

Related U.S. Application Data

[63] Continuation of Ser. No. 454,159, Dec. 21, 1989, abandoned, which is a continuation-in-part of Ser. No. 840,940, Mar. 18, 1986, abandoned.

[30] Foreign Application Priority Data

Mar. 20, 1985 [JP] Japan ................................ 60-57443

[51] Int. Cl.[5] ............................................ C12N 15/31

[52] U.S. Cl. ................................ 435/320.1; 435/69.1; 435/252.3; 536/23.2

[58] Field of Search ................ 435/252.3, 320.1, 69.1; 536/27

[56] References Cited

U.S. PATENT DOCUMENTS 4,328,313 5/1982 Simonson et al. .................. 435/200

4,438,093 3/1984 Shimada et al. ...................... 424/50

OTHER PUBLICATIONS

Cantwell, et al., *Gene*, 23:211–219 (1983).

Meyer, et al., *J. of General Microbiology*, 118:197–208 (1980).

Svanberg, et al., *Archs. Oral. Biol.*, 31(1):1–4 (1986).

J. Gen. Microl. 1301 1285–1291 (1984) Hinchliffe Cloning and Expression of a Bacillus subtilis Endo-1,3-1,-4-β-D-Glucanase Gene in *Escherichia coli* K12.

Agr. Biol. Chem. 44:1191–1192 (1980) Okami et al. A New Glucanase Produced by a Marine Bacillus.

*Primary Examiner*—Robert J. Hill, Jr.

*Assistant Examiner*—John D. Ulm

*Attorney, Agent, or Firm*—Marshall, O'Toole, Gerstein, Murray & Borun

[57] ABSTRACT

Disclosed is the isolation and cloning of genes encoding glucanohydrolase enzymes and the expression and secretion of exogenous glucanase gene products in host cells.

2 Claims, 32 Drawing Sheets

EFFECT OF pH ON THE ENZYME ACTIVITY OF α-1,3-GLUCANASE I pH STABILITY TEST OF α-1,3-GLUCANASE I

EFFECT OF THE TEMPERATURE ON THE ENZYME ACTIVITY OF α-1,3-GLUCANASE I

TEMPERATURE STABILITY TEST OF α-1,3-GLUCANASE I

SEQUENCE OF α-1, 3-GLUCANASE GENE FROM
BACILLUS CIRCULANS BC-8 (3.0 KB)

```
         10        20        30        40        50        60        70
GAATTCGGAATTGATATTGGCGATGTGACCTATTCGGCAGTTGAAGTCGATGACGACGACTGGGCTACGG

         80        90       100       110       120       130       140
CATGGAAGCAGTATTTCAAGCCGATCCGCGTATCGGAGACGTTGACCATCAAGCCGACATGGGAGGAATA

        150       160       170       180       190       200       210
CGAGGCAGGCGAAGGGGAACGCATTATTGAGCTTGATCCCGGCATGGCCTTCGGCACCGGCACGCATCCG

        220       230       240       250       260       270       280
ACGACGGCGCTCTGCTTGCAGACGCTGGAGTCGGTCGTCCAGGGCGGGCGAAGAAATGATCGATGTAGGC

        290       300       310       320       330       340       350
ACAGGCTCCGGCATTCTTCCAATCGGTGCTTGCCGACTGGGAGTGAAGGGCGTGCTTGCGCTTGATCTGG
```

FIG. 11A

```
        360        370        380        390        400        410        420
ACCCTGTTGCGGTATCCAGCGCGACGGAGAATGTGCGGCTGAACGGCTTGTCCGATCAAGTAGAAGTGAA

        430        440        450        460        470        480        490
GCTGAGCGATCTGCTTGGCGTGTTGAAGGGCGGCGAGTCTGCACCTGTTGGCAGCCATGGATTGCGCGTC

        500        510        520        530        540        550        560
ACCGTACCGGTAGATCTGGTTGTTGCCAATATTCTTGCCGAGATTATTTTGCTCTTCATCGACGACGTCT

        570        580        590        600        610        620        630
ATCAATCGCTGAAGCCAGGGCGCACATACATTGCGTCTGGTGTCTATAAGAATAAAGAAACGGATGTGGA

        640        650        660        670        680        690        700
GCAAGGTCTCATCGCCTCTGGCTTCCATATCGTAGAAAAACGCCGCGACGAGGACTGGATTGCCTTTGTT

        710        720        730        740        750        760        770
GCGAAAAAACCGCAGGAGGGATAAATGGAACGTTTCCTATGGTATCCGCTTGAGGATTTGCCGTTTATCG
```

FIG. 11B

```
       780       790       800       810       820       830       840
TCATTGTGCTCATGATTGTGTTCACGGTGCATGAATTTGCCCATGCGTACGCGGCCTATAAGTTCGGGGA

       850       860       870       880       890       900       910
CGATACGGCTTACAAAGAAGGCCGGGTTACGCTCAATCCGATGGTTCATCTGGACTTGTTCGGCTCGATC

       920       930       940       950       960       970       980
TTGCTGCTGATCGCCGGCTTTGGCTGGGCCAAGCCTGTTCCGGTCAATACAAGCCGATCAAAAATCGCCG

       990      1000      1010      1020      1030      1040      1050
ACTGATGACCATCATTGTGTCCGCTGTGGGCCCTCTGAGCAATTTGCTGATGGCTTTTATCGGGATGCTG

      1060      1070      1080      1090      1100      1110      1120
ATTTTCTATATTTTGCATGAGACAGGAGTCCTGTACTCCGCATCGCATGGCGTATATATGGCGCTTGTTC

      1130      1140      1150      1160      1170      1180      1190
ATTTCTTTTATTATTTGATCATTATTAATATTCTTTTGTTCGTCTTTAACTTTATTCCGCTGCCTCCTTT
```

FIG. 11C

```
       1200      1210      1220      1230      1240      1250      1260
GGACGGTTACCGGATTGTAGCCGAGCTGTTGCCGCTGCGTATCCGTTACAAGATCGAACAAAATATCCAT

       1270      1280      1290      1300      1310      1320      1330
TGGGCCATGATTATCTTTTTGCTGTTCGTATTCATTCCGCCGCTGCGCAGTAACGCTTGATCCGATTT

       1340      1350      1360      1370      1380      1390      1400
TGAGCCTGCAAGACCGATTTTCATAGGATTCATCAATTTCTTTGACGGCATCTTCTCGCTCTTAACTGGT

       1410      1420      1430      1440      1450      1460      1470
ACGACATTGCAATAGATTTCAGTGGTCAAAACATGCTAAGATGAAGGATGGAATAAACGTCTATGCAACG
                                                                  MetGlnArg

       1480      1490      1500      1510      1520      1530      1540
ATATTTTGTAGCGCTGACGAATTCAGCGATGCGCATTACGATAACGGGCGAGGATGCCACCATGCGGCTA
 TyrPheValAlaLeuThrAsnSerAlaMetArgIleThrIleThrGlyGluAspAlaThrMetArgLeu
```

FIG. 11D

```
       1550       1560       1570       1580       1590       1600       1610
GGGTCCATGCGCATGAAGGCGGATGATAAGCTGATCCATCCGACGGATCAGCCGATCGCCGCTGGGCCGT
GlySerMetArgMetLysAlaAspAspLysLeuIleHisProThrAspGlnProIleAlaAlaGlyProSer

       1620       1630       1640       1650       1660       1670       1680
CCCAAATCTCGCCTCAGGAAGTGAAAGCGGAAGTGCTGGAGCTACGCTGGAAAGCGAGCCGGCATGGTCG
  GlnIleSerProGlnGluValLysAlaGluValLeuGluLeuArgTrpLysAlaSerArgHisGlyArg

       1690       1700       1710       1720       1730       1740       1750
TTTGACGATCGCCCAGAGCTTCGCGAAGGGCGACAAGATGGAGCTGGTCATTCAGAAAGGGCACCGAGAT
 LeuThrIleAlaGlnSerPheAlaLysGlyAspLysMetGluLeuValIleGlnLysGlyHisArgAsp

       1760       1770       1780       1790       1800       1810       1820
CGGAGCGGCTGCGTTCCTGCCCTTCGAATCGGAACGGATGATCGTCCAGTACGATGCCAAGAAGGAAGCG
ArgSerGlyCysValProAlaLeuArgIleGlyThrAspAspArgProValArgCysGlnGluGlySerGlu

       1830       1840       1850       1860       1870       1880       1890
AACGGGCTGGAGCGCTGGGGCAAGATCGCGAAGGAGGTCGGAGCAGTCCCATCGCCATCGCATCCCGTCT
  ArgAlaGlyAlaLeuGlyGlnAspArgGluGlyGlyArgSerSerProIleAlaIleAlaSerArgLeu
```

FIG. 11E

```
    1900      1910      1920      1930      1940      1950      1960
ATCTTGCCATTTGCAAGCTGGAAAAATTGCTTGCCGGCATTGCGGAGTAACCTGGCACTGTTTTGCTATG
 SerCysHisLeuGlnAlaGlyLysIleAlaCysArgHisCysGlyValThrTrpHisCysPheAlaMet

    1970      1980      1990      2000      2010      2020      2030
AGCGAGAGGGACATAGCGCGCATGCCAGGGCATAGGCGACGTACGAGCTTGGAAGCAAGAGCGAGAGGGA
SerGluArgAspIleAlaArgMetProGlyHisArgArgArgThrSerLeuGluAlaArgAlaArgGlyArg

    2040      2050      2060      2070      2080      2090      2100
GATACGGGCACGATAAGAGTGCACATCCTTGCATCTTGCTGATCGTCGGCTGCCGAAGGCGGCTTTACAG
  TyrGlyHisAspLysSerAlaHisProCysIleLeuLeuIleValGlyCysArgArgArgLeuTyrArg

    2110      2120      2130      2140      2150      2160      2170
AGCGCGAACGCGAAGCCAAGCGGCCGGTGCTAGGCTGACCGGTCTGGGCAAACGCATATTAAGGACGGAA
 AlaArgThrArgSerGlnAlaAlaGlyAlaArgLeuThrGlyLeuGlyLysArgIleLeuArgThrGlu

    2180      2190      2200      2210      2220      2230      2240
ACGGCAGGGCTGGTTGGTTTGACCTGCCTACTATATGAATCTGGAGAAATGGGAGGAGCGGTGACAAGTA
ThrAlaGlyLeuValGlyLeuThrCysLeuLeuTyrGluSerGlyGluMetGlyGlyAlaValThrSerMet
```

FIG. 11F

```
    2250      2260      2270      2280      2290      2300      2310
TGCCAACAGTCGCGTTTTATACACTGGGCTGCAAAGTAAACTTCTACGATACGGAAGCGATTTGGCAGCT
 ProThrValAlaPheTyrThrLeuGlyCysLysValAsnPheTyrAspThrGluAlaIleTrpGlnLeu

    2320      2330      2340      2350      2360      2370      2380
ATTCAAAAATGAAGGGTACGAGCAGGTTGATTTCGAGACGACAACAGCTGACGTCTACTTAATTAATACT
 PheLysAsnGluGlyTyrGluGlnValAspPheGluThrThrThrAlaAspValTyrLeuIleAsnThr

    2390      2400      2410      2420      2430      2440      2450
TGCACCGTAACGAATACAGGAGATAAGAAGAGCCGTCAAATTATCCGCAGGCGATCAGACGCAATCCGGA
CysThrValThrAsnThrGlyAspLysLysSerArgGlnIleIleArgArgArgSerAspAlaIleArgMet

    2460      2470      2480      2490      2500      2510      2520
TGCCATTATTGCAGACGGGCTGCTATGCGCAGACATCACCGGCAGAGATTATGGCGATCGAGGGTGTCGA
 ProLeuLeuGlnThrGlyCysTyrAlaGlnThrSerProAlaGluIleMetAlaIleGluGlyValAsp

    2530      2540      2550      2560      2570      2580      2590
CCTTGTCATCGGCACACAGGATCGGGACAAAATTATGACATTTGTGAAGCAAATTCAGGATGACCGCAAG
 LeuValIleGlyThrGlnAspArgAspLysIleMetThrPheValLysGlnIleGlnAspAspArgLys
```

FIG. 11G

```
      2600      2610      2620      2630      2640      2650      2660
CCGGTCAATGGTGTGCGCAACATTATGAAGACGCAGCTTTTGAAGAGCTGGACGTGCCTGACTTTGCAGA
ProValAsnAlaValArgAsnIleMetLysThrGlnLeuLeuLysSerTrpThrCysLeuThrLeuGlnAsn

      2670      2680      2690      2700      2710      2720      2730
ACGCACGCGCGCTTTTGAAGATTCAAGAGGGCTGCAACAACTTCTGCACGTTCTGCATTATTCCATGGTC
 AlaArgAlaLeuLeuLysIleGlnGluGlyCysAsnAsnPheCysThrPheCysIleIleProTrpSer

      2740      2750      2760      2770      2780      2790      2800
GCGCGGATTGTCGGCAGCCGCGAGGCAGAGCGTACTAGAGCAGGCAAAGGCCTTAGTTGCTGCTGGCTAC
 ArgGlyLeuSerAlaAlaAlaArgGlnSerValLeuGluGlnAlaLysAlaLeuValAlaAlaGlyTyr

      2810      2820      2830      2840      2850      2860      2870
AAGGAAATCGTGCTGACGGGCATCCATACTGGCGGCTACGGCGACGATATGGAAAATTACAATTTGACAA
LysGluIleValLeuThrGlyIleHisThrGlyGlyTyrGlyAspAspMetGluAsnTyrAsnLeuThrSer

      2880      2890      2900      2910      2920      2930      2940
GCCTGCTATGGGACCTCGACAAAGTCGAAGGTTTGGAGCGGATCCGGATCAGCTCGATCGAGGCAAGTCA
 LeuLeuTrpAspLeuAspLysValGluGlyLeuGluArgIleArgIleSerSerIleGluAlaSerGln
```

FIG. 11H

```
       2950       2960       2970       2980       2990       3000       3010
AATTGATGATGCGATGATTGAAGTGCTGAACCGTTCCAGCAAGATGTGCCGCCATCTGCATATTCCGTCG
 IleAspAspAlaMetIleGluValLeuAsnArgSerSerLysMetCysArgHisLeuHisIleProSer

       3020       3030       3040       3050       3060       3070       3080
CAAGAGCAGGAGAGAATTCGGAATTTGATATTGGCGATGTGACCTATTCGGCAGTTGAATCGATGACGAC
GlnGluGlnGluArgIleArgAsnLeuIleLeuAlaMet***

       3090       3100       3110
GACTGGGCTACGGCATGGAAGCAGTATTTCAAGC
```

FIG. 11I

DEXTRANASE ACTIVITY UNDER VARIOUS pH CONDITIONS

STABILITY OF DEXTRANASE UNDER VARIOUS pH CONDITIONS

DEXTRANASE ACTIVITY AT VARIOUS TEMPERATURES

STABILITY OF DEXTRANASE AT VARIOUS TEMPERATURES

RESTRICTION MAPS OF pDEX001, pDEX002, pDEX003 AND pDEX011

RESTRICTION ENZYME MAP OF CB-8 DEXTRANASE CODING REGION AND SEQUENCING STRATEGY

SmaI DEXTRANASE GENE CARTRIDGE

SEQUENCE OF DEXTRANASE GENE FROM
ARTHROBACTER SP. CB-8 (2. 38 KB)

```
       10        20        30        40        50        60        70
GAATTCCTGGGTCGTCCGGGCGAACTTCGACGAGCGGACGAGGTGGATCGTGCGCACATCTCTCCGAATG

       80        90       100       110       120       130       140
GTGATTGCTCGCCCAGTGTGCAGCCTGATGACGATCGCGTTGCTTCTGCTCACGGCCTGGGCCTGGTACA

      150       160       170       180       190       200       210
CGTGGCCGGGAATACTCATGGCCTTCGGCTTCGCCCTGCCGCTGTTCGCCACCGTTATCGTCGTCTACTC

      220       230       240       250       260       270       280
ATTCGGTCGGTTGCCGGGAATGGACGTAGATGATCAGGCGCGCCCAAATGGAGCTACGGCCTTGGGGGGT

      290       300       310       320       330       340       350
GGTTCTCCGCTGCACCGCATAGCGACTCCGCAAGCACCAGTCCATTGACGAGAGGAACCATCATGCCCGG
                                                                 MetProGly
```

FIG. 18A

```
      360       370       380       390       400       410       420
AACAGGGCTAGGCCGGCTGGCCAAACGCATGACAGCGGCAGCCGCAGTTTTCTTTATCAGCACCAGCGCC
 ThrGlyLeuGlyArgLeuAlaLysArgMetThrAlaAlaAlaAlaValPhePheIleSerThrSerAla

      430       440       450       460       470       480       490
GTGCTCCCGGCACAGGCTGCCACCGCACCGGCAGCCGCCCCACCAGGGGTACCTGCAGCTCTCAAGGCAG
ValLeuProAlaGlnAlaAlaThrAlaProAlaAlaAlaProProGlyValProAlaAlaLeuLysAlaGlu

      500       510       520       530       540       550       560
AACGCGCCATCACAACCGTCGACAATGGCAACCTGCACACGTGGTGGCACGACAATGGCGTTTTCAGCCC
  ArgAlaIleThrThrValAspAsnGlyAsnLeuHisThrTrpTrpHisAspAsnGlyValPheSerPro

      570       580       590       600       610       620       630
AGCCACTCCAACACAAAGCAGCGAGGTTCGCCGGTCGTCCTTCTACGATGTGCAGGTTGCCCAGGCTAAT
 AlaThrProThrGlnSerSerGluValArgArgSerSerPheTyrAspValGlnValAlaGlnAlaAsn
```

FIG. 18B

```
        640        650        660        670        680        690        700
CAGCCGCAGAAGCTATACGACGCCTTCAGCTACATGAGCATTCCCCGCAGCGGAAAGGGCAAGATCGGCT
GlnProGlnLysLeuTyrAspAlaPheSerTyrMetSerIleProArgSerGlyLysGlyLysIleGlyTyr

        710        720        730        740        750        760        770
ACACAGAGGAAGACGGCGCTGAATTCTCCTCTGACGCCCGGCTTACGATGAGCTGGTCCAGCTTCGAGTA
  ThrGluGluAspGlyAlaGluPheSerSerAspAlaArgLeuThrMetSerTrpSerSerPheGluTyr

        780        790        800        810        820        830        840
CGCCAAGGACGTCTGGGTGGAAGTGAGCCTGCGCACTGGACAGACCATCTCCTCAGCCGACCAGGTCCAG
 AlaLysAspValTrpValGluValSerLeuArgThrGlyGlnThrIleSerSerAlaAspGlnValGln

        850        860        870        880        890        900        910
ATCCGGCCGAGCAGCTACAACTTTGAAAAGCAGCTCGTGGATGCAGACACTGTCAGAATCAAGGTGCCCT
IleArgProSerSerTyrAsnPheGluLysGlnLeuValAspAlaAspThrValArgIleLysValProTyr
```

FIG. 18C

```
      920       930       940       950       960       970       980
ACTCTGACGCGGGCTACAGGTTTTCGGTCGAATTTGAGCCGCAGCTTTACACCGCCTACAACGACATGAG
  SerAspAlaGlyTyrArgPheSerValGluPheGluProGlnLeuTyrThrAlaTyrAsnAspMetSer

      990      1000      1010      1020      1030      1040      1050
CGGCGACAGCGGCAAACTGACGACCGAGGCGGCCGGCAACCGGCCCATCCACACCGAGCCACGCAATTCG
 GlyAspSerGlyLysLeuThrThrGluAlaAlaGlyAsnArgProIleHisThrGluProArgAsnSer

     1060      1070      1080      1090      1100      1110      1120
ATGATGGTCTTCGCCGAACCGAAGCTTCGGGGCGAGCAGAAGGAACGACTGGTCCCGACAGAAGAGTCGG
MetMetValPheAlaGluProLysLeuArgGlyGluGlnLysGluArgLeuValProThrGluGluSerGly

     1130      1140      1150      1160      1170      1180      1190
GCAGCATCCACTATCCGGAGCCCGGCGAGGTGCGGAACCTGAACTCGGTCAGCGAGGAAATCATCTACTT
  SerIleHisTyrProGluProGlyGluValArgAsnLeuAsnSerValSerGluGluIleIleTyrPhe
```

FIG. 18D

```
       1200      1210      1220      1230      1240      1250      1260
CCGGCCCGGCACCTACAGCATGGGCCCGGACTACCATGCAGTCCTGCCAGCCAACGTGAAATGGGTCTAT
 ArgProGlyThrTyrSerMetGlyProAspTyrHisAlaValLeuProAlaAsnValLysTrpValTyr

       1270      1280      1290      1300      1310      1320      1330
CTGGCACCAGGGGCCTACGTGAAGGGAGCCTTCCGGTTCCTCCACGACACCCAAAGCCAGTACAAGGTCA
LeuAlaProGlyAlaTyrValLysGlyAlaPheArgPheLeuHisAspThrGlnSerGlnTyrLysValThr

       1340      1350      1360      1370      1380      1390      1400
CCGGATACGGCGTCCTCTCCGGCGAGCAGTACGTCTACGAGGCGGATACGAACAACAGTTACCACCACCT
  GlyTyrGlyValLeuSerGlyGluGlnTyrValTyrGluAlaAspThrAsnAsnSerTyrHisHisLeu

       1410      1420      1430      1440      1450      1460      1470
GAGCGGGGCGTCCAACTGCCACTCGTCCTGTGTAAAGATGCTGCAGTTCGCTTCCGCCGACGCGGAGCAG
 SerGlyAlaSerAsnCysHisSerSerCysValLysMetLeuGlnPheAlaSerAlaAspAlaGluGln
```

FIG. 18E 1480 1490 1500 1510 1520 1530 1540
AAGCTGGACCTGCAGGGCGTTACAGTCGCCGAGCCACCGTACCACTCCTTCGTGGTCTACGGGAACGAGC
LysLeuAspLeuGlnGlyValThrValAlaGluProProTyrHisSerPheValValTyrGlyAsnGluGln 1550 1560 1570 1580 1590 1600 1610
AAACATTCCACATGAACGTGGAGAACTACAAGCAGGTGGGCAGCTGGTACTGGCAGACAGACGGCATCGA
ThrPheHisMetAsnValGluAsnTyrLysGlnValGlySerTrpTyrTrpGlnThrAspGlyIleGlu 1620 1630 1640 1650 1660 1670 1680
GCTGTACAAAGGCAGCACCATGAAGAACACGTTCTTCAATGCCAACGACGACGTGCTGAAGATGTATCAC
LeuTyrLysGlySerThrMetLysAsnThrPhePheAsnAlaAsnAspAspValLeuLysMetTyrHis 1690 1700 1710 1720 1730 1740 1750
AGTGATGTCACCATCGATAACACGGTGATCTGGAAGAACGAGAACGGCCCCGTGATCCAGTGGGGCTGGA
SerAspValThrIleAspAsnThrValIleTrpLysAsnGluAsnGlyProValIleGlnTrpGlyTrpThr

FIG. 18F

```
    1760      1770      1780      1790      1800      1810      1820
CGCCACGGAACATTGACAACGTGAACGTCGCCAACACCACGGTCATCCACAACCGGATGTATTGGAAGGA
 ProArgAsnIleAspAsnValAsnValAlaAsnThrThrValIleHisAsnArgMetTyrTrpLysAsp

    1830      1840      1850      1860      1870      1880      1890
CGTCAAGTACAACACCTGCATCTTCAATTCCTCCTCGCACTGGGAGGACATGGGTTCCACCACCAAAGCG
 ValLysTyrAsnThrCysIlePheAsnSerSerSerHisTrpGluAspMetGlySerThrThrLysAla

    1900      1910      1920      1930      1940      1950      1960
GATCCCAACACCACGGTGAAGAACATGCGGTTCGAAAACACCGCCGTCGAAGGCATGACGAACTGCGCTA
AspProAsnThrThrValLysAsnMetArgPheGluAsnThrAlaValGluGlyMetThrAsnCysAlaIle

    1970      1980      1990      2000      2010      2020      2030
TCCGCGTCTATGCCCTGTCCGACACTGAAAACATCCACATCAAGAATTTCAACATCGGTGCCTGGAACGG
  ArgValTyrAlaLeuSerAspThrGluAsnIleHisIleLysAsnPheAsnIleGlyAlaTrpAsnGly
```

FIG. 18G

```
       2040      2050      2060      2070      2080      2090      2100
GCTGGAATGGACTTCACAGGTCAGCCACCTCAAGCGCTACACCAACTCCGCCGGTGAGAAGGTCACTATC
 LeuGluTrpThrSerGlnValSerHisLeuLysArgTyrThrAsnSerAlaGlyGluLysValThrIle

       2110      2120      2130      2140      2150      2160      2170
GGCAACGAGGTTCCCGACGGCAACGGACTCGCCCTTGAAAACTACTCAGTGGGCGGCCAAGTCATCGAGA
GlyAsnGluValProAspGlyAsnGlyLeuAlaLeuGluAsnTyrSerValGlyGlyGlnValIleGluLys

       2180      2190      2200      2210      2220      2230      2240
AGACCGGCGGAAACTCGTCAGACTACCAGCTCGGCCGGCTTGGCTTCGACGGCGAAAACTGGGAAAACTG
  ThrGlyGlyAsnSerSerAspTyrGlnLeuGlyArgLeuGlyPheAspGlyGluAsnTrpGluAsnTrp

       2250      2260      2270      2280      2290      2300      2310
GAACGCCTGGAAGTCAGCTCCCTAGCAGGCTCTCACCGAGCTCAATCCGGCGGTGAAAGTGGGCAGAGGC
 AsnAlaTrpLysSerAlaPro***

       2320      2330      2340      2350      2360      2370      2380
AAGAGTAATTCCCCACTTCCTCCAAAACAATGCAGCCAGTCAACCGGCCCTGGTGCAACTGAGCACAAAT
```

FIG. 18H

CONSTRUCTION OF pMNK-1

CONSTRACTION OF pMNK-2

```
         PstI                    HhaI              SalI
                   PROMOTER    SIGNAL SEQUENCE   INITIAL SEQUENCE
                   OF gtfB     OF gtfB           OF DEXTRANASE
```

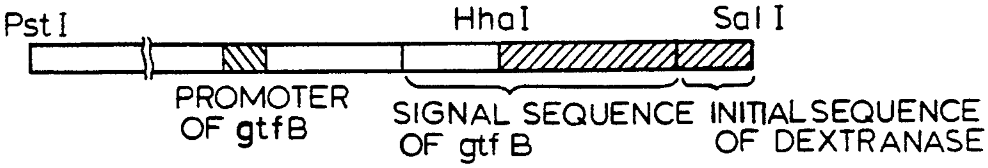

FIG. 22A

```
HhaI
5'       CAAAGTTAAAAAAAGATGGGTGACAGTATCTGTTGCATCTGCT
         GCGTTTCAATTTTTTTCTACCCACTGTCATAGACAACGTAGACGA
```
← LATE SIGNAL SEQUENCE OF gtfB GENE

```
GTGATGACTTTAACTACACTTTCGGGTGGCGAACGC
CACTACTGAAATTGATGTGAAAGCCCACCGCTTGCG
```

```
GCCATCACAACCG
CGGTAGTGTTGGCAGCT   → SalI
```
INITIAL SEQUENCE
OF MATURE DEXTRANASE
GENE

FIG. 22B

DNA ENCODING GLUCANASE ENZYMES

This is a continuation-in-part of copending U.S. Pat. application Ser. No. 06/840,940, filed Mar. 18, 1986, now abandoned.

BACKGROUND

The present invention relates generally to recombinant methods and materials useful for securing the microbial expression of exogenous gene products.

*Streptococcus mutans*, which causes caries, adheres to the surface of tooth enamel through the synthesis of extracellular polysaccharide polymers from sucrose. The most important of these polysaccharides are the glucans. One type of bond contained in glucans is the α-1,6 bond (see FIG. 1) which is similar to that of the classical dextrans. A second type of bond contained in glucans is the α-1,3 bond which is less water soluble. *S. mutans* and other cariogenic microorganisms cause tooth decay by adhesion to the tooth surface and secretion of organic acids and other material which causes demineralization of the inorganic component of tooth structure and dissolution of the residual organic matrix.

In the past, dental plaque (which is a complex of cariogenic bacteria, insoluble glucans and other material) has been mechanically removed by brushing the teeth with a tooth brush and use of materials such as dental floss. It is significant, however, that bacteria sorb rapidly to the enamel surface within minutes after the teeth are vigorously cleaned and that macroscopically visible colonies will then appear within one or two days. In addition, it is extremely difficult to ensure thorough cleaning of the teeth as dental plaque will often remain intact in areas difficult to reach with a tooth brush or dental floss.

Recently, dentifrices have been developed which provide for the enzymatic decomposition of the α-1,3 and α-1,6 glucosidic bonds holding together insoluble glucan polymers. Such dentifrices typically comprise α-1,6-glucan 6-glucanohydrolase (α-1,6 glucanase or dextranase and hereinafter referred to as dextranase) or α-1,3-glucan 3-glucanohydrolase (α-1,3 glucanase or mutanase and hereinafter referred to as α-1,3 glucanase). Simonson, et al., U.S. Pat. No. 4,328,313 and Guggenheim, et al., U.S. Pat. No. 4,353,891 each disclose methods for production of plaque dispersing α-1,3 glucanase enzyme. Shimada, et al., U.S. Pat. No. 4,438,093 discloses an oral composition for the prevention and suppression of oral diseases comprising both α-1,3 glucanse and dextranase in a pharmaceutically acceptable carrier. The application of dentifrices containing enzymes for the disintegration of such insoluble glucan is not-expected to have significant effects in decomposing dental plaque lasting beyond the period of brushing because most of the enzymatic components of the dentifrices tend to be lost during the rinsing which typically follows brushing.

Prior to the filing of parent application Ser. No. 06/840,940 herein, there had been no reports of the use of recombinant methods in the cloning and isolation of genes coding for α-1,3 glucanase or dextranase enzymes. Since that time, the cloning and expression in *E. coli* of a gene encoding the dextranase product (EC 3.2.1.70) of *Bacteroides oralis* Ig4a has been reported-See, Derwent, Biotechnclogy Abstracts 88-00247 and 88-01356 (1988).

From the above description of the state of the art it is apparent that there exists a need in the art for improved methods and materials providing glucanase activity in the human oral cavity. Such methods and materials should preferably provide consistent long lasting glucanase activity and should preferably not require frequent application.

SUMMARY OF INVENTION

The present invention provides purified and isolated DNA sequences encoding α-1,3 glucanase and dextranase. More particularly provided is the isolated DNA sequence coding on expression for the approximately 68 kD α-1,3 glucanase II enzyme (EC 3.2.1.59) of the newly discovered *Bacillus circulans* BC-8 which is deposited with the Fermentation Research Institute of Microbial Industry, Agency of Industrial Science and Technology, Japan, under accession number FERM BP-733. Correspondingly provided is the isolated DNA sequence coding on expression for the approximately 62 kD dextranase enzyme (EC 3.2.1.11) of newly discovered Arthrobacter sp. CB-8,similarly deposited under accession number FERM BP-995. These DNA sequences and fragments thereof encoding expression of polypeptide products are conspicuously useful in the recombinant production of enzymatically active products and also useful as hybridization probes for the isolation from other organims (under stringent conditions) of DNA sequences and fragments encoding polypeptides having, by virtue of polypeptide homology, the same biological properties and activity.

In one of its aspects, therefore, the present invention provides recombinant DNA molecules consisting of DNA from different genomes which have been joined end-to-end outside of living cells and which have the capacity to transform a host and to be maintained therein, and in the progeny thereof, comprising a DNA sequence selected from the group consisting of DNA fragments encoding either α-1,3 glucanase or dextranase, and DNA fragments which hybridize under stringent hybridization conditions to the foregoing DNAs and which respectranase activities. Also provided are hosts transformed with DNA molecules coding for the expression of α-1,3 glucanase and dextranase enzyme activities. Specifically illustrated are *Escherichia coli* and *Streptococcus* hosts.

Specifically, aspects of the invention comprise: (1) cloning genes of a bacterium which produces α-1,3 glucanase, dextranase, or both of them, 2) transforming bacterial cells of a type indigenous to the oral cavity (e.g., *Streptococcus sanguis*), with such genes so as to allow for expression and secretion of the gene products. Use of both α-1,3 glucanase and dextranase in combination produces a synergistic effect in degrading the insoluble glucan materials making up dental plaque. Accordingly, genes coding for the expression and secretion of both types of glucanase may be introduced separately or together into the same or different transformed bacteria of the type indigenous to the oral cavity.

DNA sequences of the present invention are suitably employed in the construction of autonomously replicating vectors by insertion of the sequence into the vector at one or two restriction endonuclease recognition sites therein. Such vectors preferably include appropriate expression control sequences and allow the stable transformation of host cells in a manner permitting enzyme synthesis (i.e., by DNA transcription to mRNA and mRNA translation to polypeptides) as well as the intracellular processing and secretion of enzyme products in biologically active form. Vectors provided according to the present invention may thus include, in addition to DNA encoding α-1,3 glucanase or dextranase enzymes, suitable promoter DNA sequences facilitating mRNA transcription, suitable ribosome binding site sequences facilitating mRNA translation, and suitable signal-encoding DNA sequences for processing and secretion of translation products. Such additional DNA sequences are preferably derived from the cloning of genes endogenous to the host cells selected for expression. Expression of desired enzymatically active products may also be achieved by direct incorporation of DNA into the genome of the selected host cells.

Other aspects of the invention will become apparent upon consideration of the following detailed description of preferred embodiments thereof.

DESCRIPTION OF DRAWINGS

FIG. 6(*b*) is a diagramatic representation of the preparation of expression plasmid pMN-3;

FIGS. 11A to I provide DNA and deduced amino acid sequence information concerning a cloned α-1,3 glucanase gene according to the invention:

FIGS. 18A to H provide DNA and deduced amino acid sequence information concerning a cloned dextranase gene according to the invention;

FIG. 22(a) and 22(b) are diagramatic representations of DNA constructions useful in practice of the invention.

DETAILED DESCRIPTION

Figure 1:
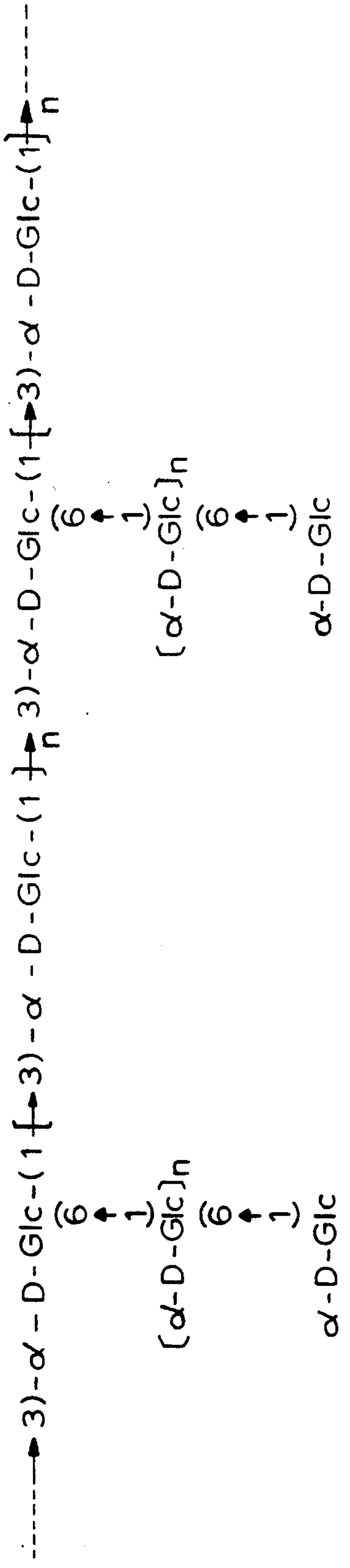
FIG. 1 shows the structure of the insoluble glucan.

The following examples illustrate isolation of bacteria expressing genes for α-1,3 glucanase and dextranase activity, characterization of these bacteria and their enzyme products, cloning and expression of genes coding for that activity, introduction of genes coding for the desired enzymatic activity into bacteria indigeneous to the oral cavity, and the expression and secretion of glucanase gene products by recombinant host cells.

EXAMPLE 1

This example relates to procedures applied to the isolation of α-1,3 glucanase and dextranase producing organisms from soil samples. In the case of isolation of α-1,3 glucanase, a sample of soil comprising weathered granite mixed with peat and having a pH of approximately 6 was obtained from the inventors garden and was added to a sterilized and phosphate buffered (pH 7) minimal medium comprising 0.1% (by weight) $(NH_4)_2SO_4$, 0.0005% $MgSO_4.7H_2O$, 0.0005% $FeCl_2.6$-$H_2O$ and 0.03% insoluble glucan obtained from cariogenic bacterium *Streptococcus mutans* strain OMZ 176 which was the sole carbon source. The method for preparing the insoluble glucan was in accordance with that of Ebisu (Osaka University Journal of Dentistry, Vol. 21, No. 1 1976). The soil samples were incubated in the medium for three consecutive days at 28° C.

A variety of bacteria cultured in the medium were subcultured twelve times and were concentrated. Agar plates were prepared comprising 1.2% (by weight) agar to which 0.2% insoluble glucan and the minimal medium described above had been added. The plates were then inoculated with the concentrated bacteria and were cultured to form colonies. After several days of incubation at 30° C., bacteria which expressed α-1,3 glucanase activity and degraded the insoluble glucan were identified by the formation of transparent halos around the colonies.

Three bacterial strains identified as expressing α-1,3 glucanase activity were cultured and characterized. Bacteria forming the most conspicuous halo were identified as *Bacillus circulans* BC-8 and were deposited with the Fermentation Research Institute of Microbial Industry, Agency of Industrial Science & Technology, Japan, under accession number FERM BP-733. The other two colonies, showing faint halos, were identified as Pseudomonas sp.

In the case of the isolation of dextranase, a sample of soil was added to a sterilized and phosphate buffered (pH 7.0) minimal medium comprising 0.1% (by weight) $(NH_4)_2SO_4$, 0.0005% $MgSO_4$, $7H_2O$, 0.0005% $FeCl_2.6$-$H_2O$ and 0.2% Dextran T70 (Pharmacia) which was the sole carbon source. The soil samples were incubated in the medium for three days at 28° C. A variety of bacteria cultured in that medium were subcultured six times and were concentrated. The concentrated bacteria were inoculated to the same plates used in the isolation of α-1,3 glucanase producing organism, containing insoluble glucan as a sole carbon source. After several days of incubation at 30° C., one bacterial strain which expressed strong dextranase activity and showed good growth by the assimilation of insoluble glucan decomposed by dextranase enzyme, was isolated. This bacteria identified as Arthrobacter CB-8 which was similarly deposited under accession number FERM BP-995.

A. Properties of BC-8

The above-mentioned Bacillus circulans BC-8 (hereinafter referred to as "BC-8") has been found to have the following bacteriological properties:

(1) Cell Characteristics

A gram-positive bacillus. Size: 0.5×1.3–2.6 μm. No motility. Forms endospores. The shape of the spore is an oblong ellipse. The spores are present on ends. The cell grows aerobically.

(2) Colony Characteristics

The bacterium forms circular and smooth pale yellowish white colonies on peptone and yeast extract agar medium.

(3) Chemical Properties

Catalase: (+);
Oxidase Weak (+);
Voges-Proskauer test: (−);
Indole production: (−);
Dihydroxyacetone production from glycerol: (−);
Reduction of nitric acid: (−);
Casein hydrolysis: (−);
Starch hydrolysis: (+);
Tyrosine hydrolysis: (−);
Gelatin hydrolysis: (−);
Growth in a liquid medium containing 0.001% lysozyme: (−);
Growth in media containing 5% NaCl: (+);
Growth in media containing 7% NaCl: (−);
The bacterium produces acid, but not gas, from glucose, lactose, mannitol, and trehalose;
The bacterium does not produce acid or gas from arabinose, fructose, mannose, and xylose;
Growth temperature: grows in the range from 17° C. to 37° C., but no growth is observed at 10° C. or 45° C.;
Vitamin requirements: biotin; and,
G+C content of DNA: 49.5 mol %.

On the basis of the above-mentioned properties, the BC-8 bacterium was found to belong to the genus of aerobic spore-forming bacillus classified as Bacillus circulans Jordan.

B. Properties of CB-8

The above-mentioned *Arthrobacter sp.* (hereinafter referred to as "CB-8") has been found to have the following bacteriological properties:

(1) Cell Characteristics

A gram-positive bacillus. The size and shape vary according to the culture conditions and culture period; 0.5×0.6∼2.0 μm. Apospory. Obligative aerobic growth.

(2) Colony Characteristics

The bacterium forms circular and smooth dark yellow colonies on peptone and yeast extract agar medium.

(3) Chemical Properties

Catalase: (+);
Hemolytic (sheep): (−);
Carbohydrate fermentability: glucose (−), lactose (−), maltose (−), mannitol (−), salicin (−), starch (−), sucrose (−), trehalose (−), xylose (−);
Voges-Proskauer test: (−);
Esquirine hydrolysis: (−);
Reduction of nitrate: (−);
Gelatin liquefaction: (+);
Urease: (+);
Arginine hydrolysis: (−);
Includes lysine as a constitutive diamino acid of peptidoglycan of cell wall; and
Quinone is menaquinone MK-9 ($H_2$) with isoprene unit number 9, 1 saturated type.

On the basis of the above-mentioned properties, CB-8 was determined to belong to the genus of Arthrobacter.

EXAMPLE 2

This example describes the cultured growth of bacterium BC-8 and the isolation therefrom and characterization of two isozymes, α-1,3 glucanase I and II. More specifically, this example addresses: general considerations relating to the cultured growth of BC-8 including suitable culture media and growth conditions; general considerations relating the isolation of said isozymes from culture media; preparation of insoluble glucans; three specific procedures for the production of α-1,3 glucanase enzyme from BC-8; and characterization of physicochemical and enzymatic properties of the isozymes.

A. General Considerations Relating to Cultured Growth of BC-8

(1) Culture Medium

For producing α-1,3 glucanase, BC-8 can be cultivated using any suitable natural or synthetic medium. For industrial production, however, it is more advantageous in terms of cost and yield to use jar fermenter culture with a liquid medium.

Nutrients for incorporation into BC-8 media are those commonly used for microorganisms. For instance, nitrogen sources include ammonium phosphate, ammonium sulfate, peptone, and yeast extract. Inorganic salts include salts of phosphoric acid, sodium, potassium, magnesium, and calcium. Insoluble glucan produced by cariogenic streptococcus is most effective as a carbon source. Insoluble glucan preparations as described in part D, below, may be added to the medium in concentration of 0.1% (W/V) or more as a carbon source and to induce enzyme production.

(2) Growth conditions

The BC-8 organism is typically inoculated on the medium prepared according to (1) above, and the bacterium is allowed to grow at the specified culture temperature, preferably within the range from 30° C. to 37° C., with pH of the medium in the range from 6 to 7, until α-1,3 glucanase reaches the highest activity in the culture fluid. The incubation period depends on the culture conditions, but is generally from one to three days for jar fermenter culture systems.

B. Harvest and Purification of α-1,3 glucanase I and II from Culture

The culture medium in which α-1,3 glucanase has been produced is typically centrifuged to remove bacterial cells and obtain a crude enzyme supernatant solution.

If insoluble glucan has been added to the medium as a culture substrate beforehand, a small amount of insoluble matter will remain at the time of completion of the culture, and α-1,3 glucanase will be adsorbed to the insoluble matter. Accordingly, an appropriate amount of a suitable dextranase is added to the medium before culture or dextranase to the culture fluid after growth to disintegrate the insoluble matter. The fluid is then centrifuged to provide a crude enzyme solution. Furthermore, it is also effective to wash the above-mentioned insoluble matter precipitated from the culture medium with a water-soluble low-molecular-weight glucan solution (the preparation of which is described in part C, below) so as to elute adsorbed α-1,3 glucanase. The liquid is then centrifuged to prepare crude enzyme solution. It is thus possible to increase the yield of α-1,3 glucanase by properly combining both dextranase treatment and water-soluble low-molecular-weight glucan treatment.

The crude enzyme solution thus obtained is fully usable without any further processing. It is also possible, however, to obtain a purified enzyme solution by applying, singly or in combination, various known purification processes, such as ultrafiltration, vacuum concentration, salting out with ammonium sulfate, solvent fractionation with ethanol, etc., isoelectric precipitation, and column chromatography.

Furthermore, α-1,3-glucanase I and II activities may be separated from glucanase preparation by applying ion-exchange chromatography with CM-Sepharose CL-6B resin (the separation of said isozyme is described infra at part D(3). As the molecular weights of said isozymes were very different, the above-mentioned separation is also possible by gel filtration technique with Bio-Gel P-200 resin or polyacrylamide gel electrophoresis.

C. Preparation of Insoluble Glucan and Low Molecular Weight Water Soluble Glucan Cariogenic streptococcus (*Streptococcus mutans* OMZ-176 strain) was inoculated on a liquid medium containing 3% of Todd Hewitt Broth (Difco), and cultured for 24 hours at 37° C. with standing (not shaking). The resulting culture medium was centrifuged to remove the bacterial cells. The culture supernatant was then subjected to salting-out with 50% saturated ammonium sulfate. The resulting insoluble matter was collected as a precipitate by centrifugation. The precipitate was dissolved in 50 mM citrate buffer (pH 6.5) and thereafter the solution was dialyzed against same buffer. The resulting dialysate was an insoluble glucan synthetic enzyme solution.

After dialysis, 10% sucrose dissolved in 50 mM citrate buffer (pH 6.5) was added to the enzyme solution as enzyme substrates, and the mixture was incubated for 24 to 48 hours at 37° C. so as to synthesize insoluble glucan. Insoluble glucan was collected by centrifugation and washed with distilled water, then with ethanol and acetone. The glucan was then dried at 100° C. to provide purified insoluble glucan preparation.

The insoluble glucan synthetic enzyme solution of cariogenic streptococcus prepared by the abovementioned method was put into a dialysis tube. The . solution was dialyzed against 50 mM citric acid buffer containing 10% sucrose at 37° C. for 24 to 48 hours under agitation; thus synthesis of low-molecular-weight glucan and dialysis were conducted at the same time.

After dialysis, the resulting outer solution contains water-soluble low-molecular-weight glucan which can be used directly for harvesting the above-mentioned α-1,3 glucanase. If necessary, ethanol may be added to the solution to 66% (v/v). The precipitate is then collected by centrifugation, washed with ethanol and acetone, and dried at 100° C. to provide a purified water-soluble low-molecular-weight glucan.

D. Methods for α-1,3-glucanase Production Using Bacillus circulans BC-8

(1) Procedure No. 1

100 ml of a liquid medium (pH 7.0), which contained 0.5% (W/V in dry weight) insoluble glucan prepared by the above-mentioned procedure, 0.5% 2-ammonium phosphate [$(NH_4)_2HPO_4$], 0.1% 1-potassium phosphate ($KH_2PO_4$), 0.1% sodium chloride, and 0.1% yeast extract (Difco), was put into an 500-ml Erlenmeyer flask with a cotton plug. After heat sterilization, 1 ml of a separately sterilized 1M magnesium sulfate aqueous solution and 1 ml of a separately sterilized 0.1M calcium chloride solution were added to that flask. Five ml of the BC-8 seed culture, which had been cultured for 24 hours with the same medium, was inoculated into the medium and the bacterium was cultured at 37° C. for 48 hours on a rotary type shaker.

An equivalent water-soluble low-molecular-weight glucan solution as described above was added to the culture fluid, and the mixture was centrifuged to obtain the culture supernatant. The activity of α-1,3-glucanase in this culture supernatant was observed to be 770 units per 1 ml of the original medium.

(2) Procedure No. 2

500 ml of a liquid medium identical to that of the above-mentioned Procedure No. 1 was put into a 3% Erlenmeyer flask with a cotton plug. The medium was sterilized by heating, and magnesium sulfate and calcium chloride were added to the medium to provide the same concentration as Procedure No. 1. Furthermore, an aqueous solution of dextranase produced by a fungus belonging to the genus of Penicillium (of Seikagakukogyosha) was aseptically filtrated and added to the medium so that 4 mg of said dextranase was present in the flask.

25 ml of a BC-8 bacterium culture fluid, which had been prepared by incubating the bacterium on a similar medium for 24 hours, was inoculated and incubated at 37° C. for 48 hours on rotary type shaker. Upon completion of growth, the culture was treated with water-soluble low-molecular-weight glucan solution in the same way as Procedure No. 1,and the culture supernatant was obtained. The activity of α-1,3 glucanase in the culture supernatant was observed to be 775 units per 1 ml of the initial medium. Where the dextranase was added to the medium in advance, there were almost no residual insoluble matter other than the BC-8 bacterium cells after the completion of culture.

(3) Procedure No. 3

A liquid medium prepared as in Procedure No. 1 was divided and put into 3 l Erlenmeyer flasks with a cotton plug; each flask was filled with 500 ml of the medium. After heat sterilization, magnesium sulfate and calcium chloride were added to the medium to provide the same concentrations as in Procedure No. 1. Then 25 ml of a BC-8 bacterium pre-culture fluid, which had been prepared by incubating the bacterium on a similar medium for 24 hours, was inoculated on the medium of each flask. The culture was incubated at 37° C. for 48 hours on rotary type shaker. 4.5 l of the culture fluid thus prepared were centrifuged to separate it into the supernatant (1) and the precipitate fraction containing BC-8 bacterium cells and glucan residue. 250 ml of water-soluble low-molecular-weight glucan solution was added to the precipitate fraction and the suspension was allowed to stand at 0° C. for 10 minutes. The suspension was then centrifuged to separate it into supernatant (2) and the precipitate fractions. 250 ml of water-soluble low-molecular-weight glucan solution was added again to the precipitate fraction, and the solution was subjected to similar treatments. As a result, supernatant (3) and precipitate fractions were separated from each other. The supernatants (1), (2) and (3) were mixed and subjected to 0–40% (V/V) ethanol fractionation. The precipitate was collected by centrifugation and was suspended in a small quantity of 50 mM phosphate buffer (pH 7.0). This suspension was dialyzed against the same buffer. After dialysis, the liquid was centrifuged to separate it into supernatant (4) and precipitate fractions. The precipitate fraction was twice subjected to a treatment as using water-soluble low-molecular-weight glucan solution (100 ml each). As a result, supernatants (5) and (6) were obtained. The supernatants (4), (5) and (6) were mixed again, and 2,000 Seikagakukogyo units of dextranase CG (available from Seikagakukogyosha) was added. The mixture was allowed to react at 37° C. for six hours and then centrifuged to separate it into supernatant (7) and precipitate fractions. The precipitate fraction was twice subjected to the treatment with 200 ml of water-soluble low-molecular-weight glucan solution (200 ml each). Centrifugation produced supernatants (8) and (9). Supernatants (7), (8) and (9) were mixed and concentrated by ultrafiltration. The concentrated liquid was dialyzed against 50 mM phosphoric acid buffer (pH 7.0) and the dialyzed liquid was then put into a sephacryl S-200 column equilibrated with the same buffer so as to elute with the same buffer. Because dextranase has an affinity for sephacryl resin, this treatment successfully eliminated the dextranase which had been added to the enzyme liquid. The eluted glucanase fraction was collected and placed on a DEAE-Sephacel column equilibrated with 50 mM phosphate buffer (pH 7.0). The α-1,3 glucanase fraction, which had not been absorbed, was eluted out by the buffer and was collected. This fraction was concentrated by ultrafiltration and dialyzed against 50 mM acetic acid buffer (pH 4.5). The dialyzed liquid was then put into a CM-Sepharose CL-6B column equilibrated with the same buffer, and the column was fully washed with a linear concentration gradient of 0–0.6M NaCl (50 mM acetic acid buffer, pH 4.5).

Most of glucanase I enzyme activity was eluted at 0.1M NaCl. The fraction having glucanase I activity was collected and applied to SDS-polyacrylamide gel electrophoresis. As a result, a single protein band at about 180 kD was detected. With the above-mentioned purification procedure, the α-1,3 glucanase I of the BC-8 was obtained in an electrophoretically pure form, with a total yield of 49,400 units (338 μg as protein) purified α-1,3 glucanase. The specific activity of the purified α-1,3 glucanase I specimen was 146,000 (unit/mg of protein).

α-1,3 glucanase II activity was subsequently eluted at 0.2M NaCl on CM-Sepharose CL-6B ion-exchange chromatography. The collected fraction of α-1,3 glucanase II enzyme was also applied to SDS-polyacrylamide gel electrophoresis. The approximately 68 kD α-1,3 glucanase II enzyme was provided as 13,000 units of activity (95 μg/protein). The specific activity of the purified α-1,3 glucanase II was 137,000 (unit/mg of protein).

E. Physicochemical and Enzymatic Properties of α-1,3 glucanase I and II

α-1,3 glucanase I and II produced by the BC-8 according to the method of production of the present invention has the following physicochemical and enzymatic properties:

(1) Molecular Weight

The molecular weights of the α-1,3 glucanase I and II were determined by the SDS - polyacrylamide gel electrophoresis to be about 180,000 and 68,000, respectively.

(2) Optimum pH and Stable pH

Figure 7:
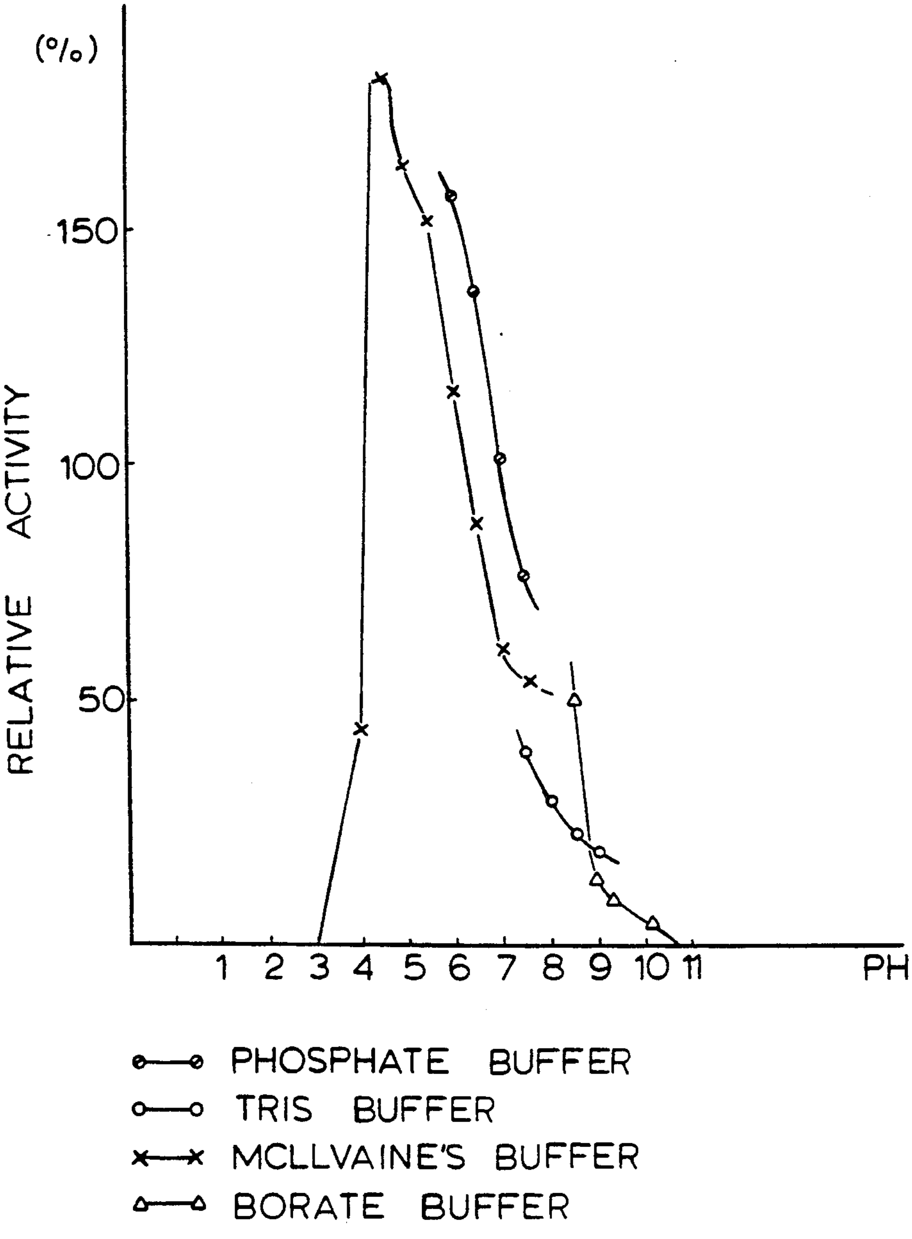
FIGS. 7 through 10 are graphic representations of results of testing of enzymatic properties of α-1,3 glucanase.

FIG. 7 shows the activity of α-1,3 glucanase I under various pH conditions and in various buffers. The relative activity in phosphate buffer, pH 7.0, was designated as 100%. The effect of pH is revealed in the curves shown in the Figure. The enzyme activity is found in a wide range from pH 4.0 to 9.0. In particular, the maximum activity is observed around pH 5.0. The activity of α-1,3 glucanase II under various pH conditions was almost the same as that of α-1,3 glucanase I.

Figure 8:
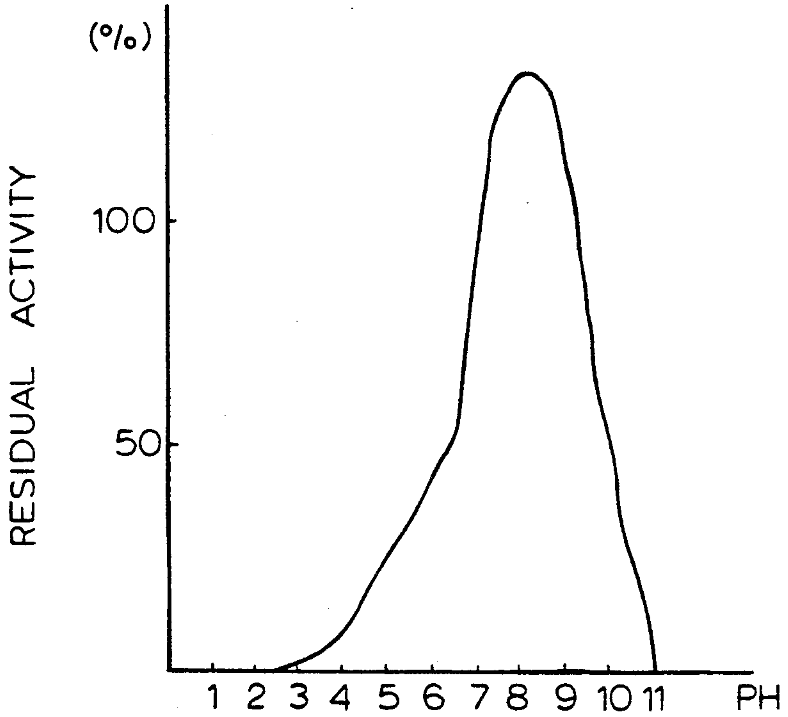

FIG. 8 shows the stability of α-1,3 glucanase I toward pH in terms of the residual activity after standing α-1,3 glucanase I at 40° C. for 5 hours under various pH conditions (the activity level with phosphate buffer, pH 7.0,without standing was regarded as 100%). As shown in the Figure, the enzyme is stable in a wide range from pH 6.0 to 10.0. In particular, it is very stable in a range from pH 7.0 to 9.0. The curve of α-1,3 glucanase II indicates essentially the same pH stability as that of α-1,3 glucanase I.

(3) Optimum Temperature and Stable Temperature

Figure 9:
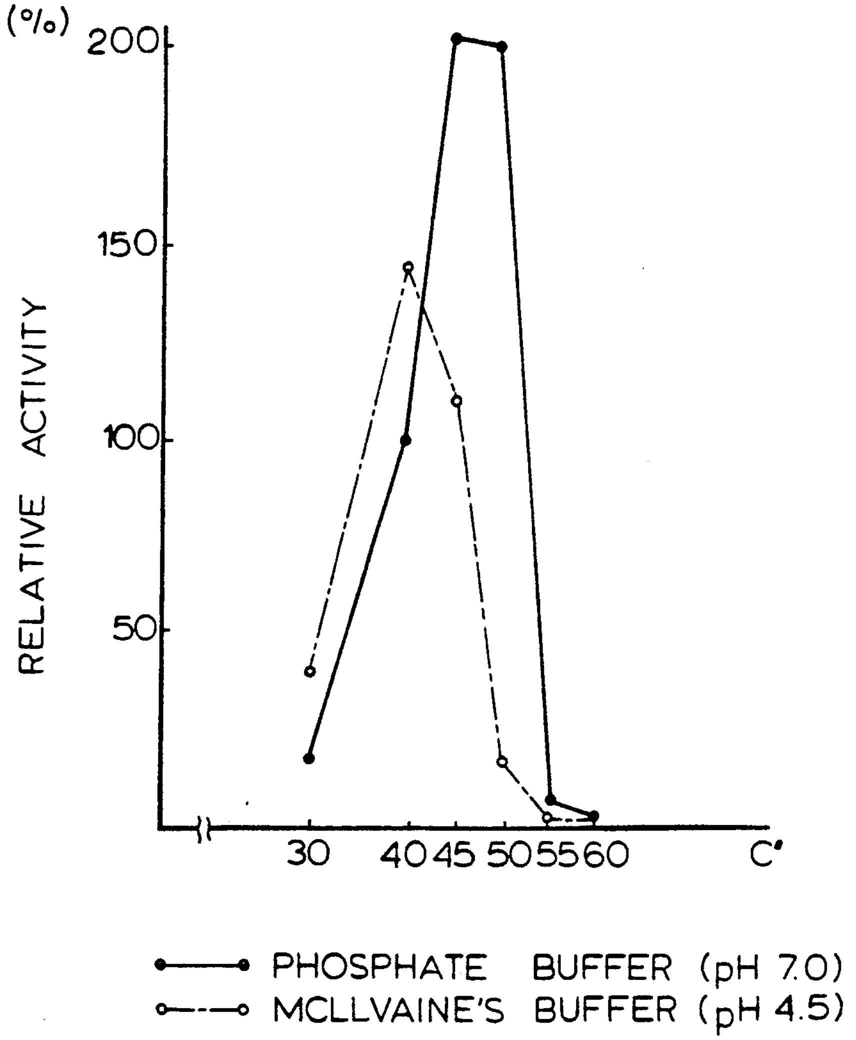

As shown in FIG. 9, the optimum temperature for enzymatic activity of α-1,3 glucanase I is 45° C. 1,3 glucanase II also shows the optimum temperature of 45° C.

Figure 10:
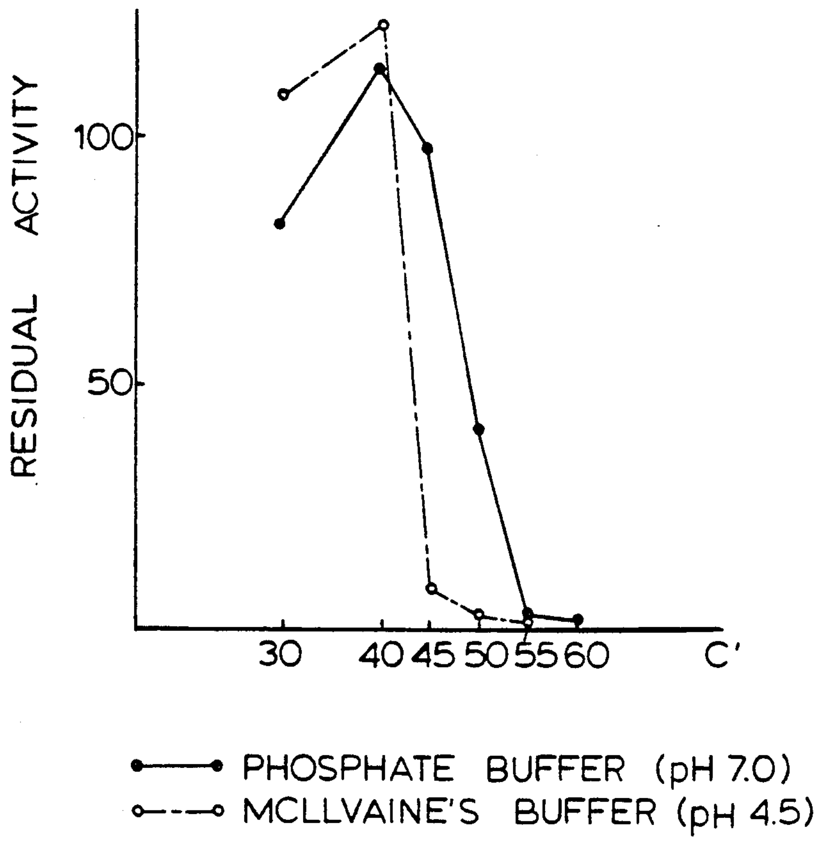

FIG. 10 shows the stability of α-1,3 glucanase I at various temperatures based on residual activity measured after standing α-1,3 glucanase I at the respective temperatures for 5 hours (the activity without standing was regarded as 100%). As shown in the Figure, the enzyme is stable at temperature below 40° C. The profile obtained in α-1,3 glucanase II was almost the same as that of α-1,3 glucanase I.

(4) Effects of Metallic Ions and Enzyme Inhibitors

Both α-1,3 glucanase I and II are inhibited by $Fe^{2+}$, $Pb^{2+}$, and $Ag^{2+}$. In particular, $Hg^{2+}$ and $Ag^{2+}$ cause a significant inhibition. pCMB (p-chloromercuribenzoic acid) also causes a significant inhibition of enzymatic activity.

(5) Actions and Substrate Specificity

α-1,3 Glucanase I and II have a property of hydrolyzing α-1,3 glucosidic linkages of insoluble glucan in the manner, of an endo type enzyme. In particular, both enzymes effectively degrade insoluble glucan produced by cariogenic Streptococcus.

(6) Method of Measuring the Activity 0.1 ml of α-1,3 glucanase solution was added to 0.2 ml of 1.3-α-D glucan suspension (6 mg/ml, 50 mM phosphate buffer, pH 7.0), and the mixture was incubated for 16 hours at 40° C. The reaction was terminated by adding ethanol (final concentration was 60%), and amount of the sugar which had become soluble in this condition was determined by the phenol sulfuric acid method.

Under the above-mentioned reaction conditions, the enzyme activity which produced an amount of sugar soluble in 60% ethanol and corresponding to 100 nmol of glucose was defined as one unit. In practice, α-1,3 glucanase solutions of various concentrations were used for developing the standard curve, and the enzyme activity was read out on it.

(7) Amino Acid Sequence

N-terminal amino acid sequence of the purified α-1,3 glucanase I protein is as follows:

Ala—Gly—Ala—Pro—Asn—Leu—Thr—Leu—Gly—Lys—Asn—Ile—Thr—

No N-terminal amino acid sequence for purified α-1,3 glucanase II enzyme has yet been developed but, as described in the following examples, it is possible to develop a deduced amino acid sequence from information provided by the nucleotide sequence of the DNA coding for the enzyme.

EXAMPLE 4

In this example, the gene coding for the expression of the BC-8 α-1,3 glucanase was cloned into an *E. coli* expression vector and transformed into *E. coli*. Bacterium BC-8 was cultured with trypticase soy broth and the DNA was extracted in accordance with the method of Marmur, *J. Mol. Biol.*, 3, 208 (1961). This material was centrifuged by the CsCl-EtBr equilibrium density gradient centrifugation method which revealed no plasmid DNA. A single band of chromosome DNA was then isolated and purified. The DNA thus purified was then dialyzed and cleaved by EcoRI restriction endonuclease.

At the same time, *E. coli* HB 101 having the commercially available expression vector pYEJ 001 plasmid (Pharmacia P-L Biochemicals, Uppsala, Sweden) (see FIG. 2) was cultured with 300 ml of L-broth [comprising 10 g peptone, 5 g yeast extract, 1 g glucose, 5 g NaCl and 1000 ml of $H_2O$ (adjusted to pH 7.2)]. The pYEJ 001 plasmid DNA was then extracted and isolated and itself cleaved by EcoRI.

One μg of the bacterium BC-8 EcoRI DNA fragments and one μg of the pYEJ 001 plasmid DNA thus obtained were then combined in the presence of one unit of T4 DNA ligase and incubated for 12 hours at 4° C. The recombinant plasmid DNA thus generated by the combination of the two DNA fragments was then dialyzed in 10 mM Tris-HCl solution (pH 7.5, 1 mM EDTA). The recombinant plasmid DNA was then transformed into *E. coli* K12 strain HB 101.

EXAMPLE 5

In this example, transformed *E. coli* K12 strain HB 101 bacteria were screened for the presence of the α-1,3 glucanase gene.

Figure 2:
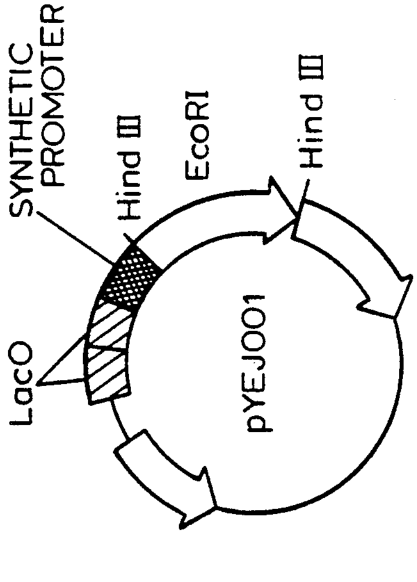
FIG. 2 is a gene map of the pYEJ 001 plasmid present in the cytoplasm of *Escherichia coli;*

As shown in FIG. 2, if a DNA fragment is inserted into the EcoRI site of the chloramphenicol resistance gene ($Cm^r$) of the pYEJ 001 plasmid, the bacterium will become sensitive to chloramphenicol. In addition, because the synthetic promoter is present upstream of this site, any gene in the DNA inserted into that site which is aligned in the proper (3′ to 5′) direction and in the proper reading frame can be strongly expressed.

Cultures of *E. coli* which were transformed with the recombinant pYEJ 001 plasmid were arranged to make colonies on agar plates containing ampicillin, and each colony was transferred by a sterilized stick to a L-agar plate (L-broth containing 1.5% agar) containing chloramphenicol (Cm). Cultures of *E. coli* showing Cm sensitivity were those into which some DNA fragment was inserted at the EcoRI site.

From among the colonies showing Cm sensitivity, it was then necessary to identify those into which the α-1,3 glucanase gene had been successfully inserted. Because, *E. coli* is a gram-negative bacterium (and unlike bacterium BC-8,is incapable of secreting the α-1,3 glucanase enzyme) no transformants were found to secrete α-1,3 glucanase out of several thousands of colonies transferred to plates containing insoluble glucan.

As the host bacterium HB 101 requires amino acids such as threonine, leucine and proline, the Cm-sensitive ($Cm^S$) *E. coli* colonies were cultivated on a synthetic minimal medium comprising a small amount of casamino acids and 0.2% ultrasonically pulverized insoluble glucan as the only carbon source. While no halos were formed and the transformants were deemed incapable of secreting the α-1,3 glucanase, the fact that some of the colonies were observed to grow indicated that they expressed the product of the a-1,3 glucanase gene and had acquired the capability to degrade and exploit the insoluble glucan as a carbon source.

Those transformants observed to grow on the minimal medium were then cultured on a slightly larger scale (1 liter), and their plasmid DNA was extracted and cleaved by EcoRI restriction endonuclease. The digested DNA was then examined by gel electrophoresis and found to contain a 3.0 kb DNA fragment. This fragment size was considered sufficient to code for a gene product with a size corresponding to the 68 kD molecular weight calculated for the α-1,3 glucanase II material.

To demonstrate that the α-1,3 glucanase gene is present in this 3.0 kb DNA fragment, various bacterial cultures were incubated in 30 ml of minimal media containing 0.2% insoluble glucan. The cultures included; (1) *E. coli* HB 101; (2) Bacterium HB 101 transformed with plasmid pYEJ 001; and (3) Bacterium Hb 101 transformed with plasmid pYEJ 001 including the 3.0 kb DNA fragment insert. The supernatant obtained from centrifugation of lysed cells from the three types of cultures was assayed for α-1,3 glucanase activity with the result that only the bacteria transformed with plasmid pYEJ 001 including the 3.0 kb fragment exhibited α-1,3 glucanase activity, thus demonstrating that the α-1,3 glucanase gene of the bacterium BC-8 had been successfully cloned into the pYEJ 001 plasmid of *E. coli*. Further, only HB 101 cells transformed with pYEJ 001 including the 3.0 kb insert were able to survive in casamino acids and insoluble glucan as described above.

A confirmation of the presence of DNA encoding the 68 kD α-1,3 glucanase II enzyme within the 3 kb fragment was provided by Western blot analysis using rabbit polyclonal antibodies (antisera) raised against α-1,3 glucanase I or II separately. Briefly, rabbits were injected with one or the other of the two isozymes isolated from BC-8 and separated by ion exchange chromatography. When antibody titers indicated the highest level, blood was collected from the rabbits. Serum fractions of the collected blood were used in the following experiments as polyclonal antibodies (antisera). Antibody titers were determined by the ELISA method of Davis et al., *Basic Methods in Molecular Biology*, 348–354 (1986). Upon Western blot analysis of cellular proteins, greater reactivity was noted with equal titers of antisera raised against α-1,3 glucanase II enzyme as opposed to that raised against α-1,3 glucanase I. The most reactive protein band migrated to the region of about 68 kD, confirming that the α-1,3 glucanase II enzyme was coded for by the 3.0 kb DNA fragment.

The 3 kb HindIII fragment was subjected to sequencing by the dideoxy chain termination method. The DNA sequence is set out in FIGS. 11A to E and reveals an open reading from base 1465 which extends nearly to the end of the fragment.

EXAMPLE 6

In this example, *Streptococcus sanguis Challis* strain (NCTC7868) a bacterium normally present in the flora of the oral cavity was successfully transformed with the gene coding for the expression of α-1,3 glucanase II. Among various bacteria indigenous to the oral cavity, *S. sanguis* and *Streptococcus salivarius* are the most innoxious bacteria, and in particular, *Streptococcus sanguis*

*Challis* strain (NCTC7868) is a host the genetics and transformation of which are relatively well understood. Plasmid pGB 301 (see FIG. 3,Behnke et al., *M.G.G. Molecular and Genetics,* 184, 115–120 (1981); Behnke et al., *Microbiology, American Society for Microbiology,* 239–242 (1982) was used as a transformation vector.

Figure 3:
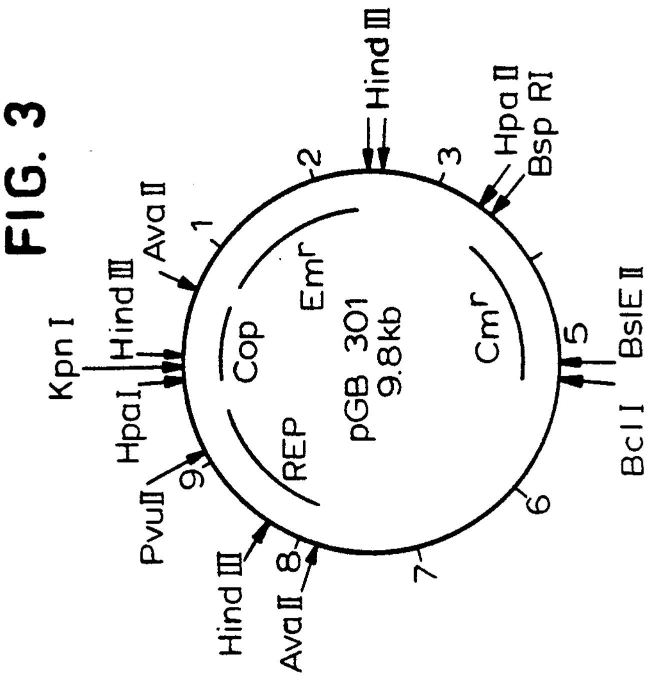
FIG. 3 is a gene map of the pGB 301 plasmid present in the cytoplasm of *Streptococcus sanguis.*

As shown in FIG. 3, the pGB 301 plasmid DNA which is present in the cytoplasm of *S. sanguis Challis* strain has two drug-resistant markers, $Em^r$ (erythromycin resistance) and $Cm^r$ (chloramphenicol resistance) with a unique Bst E II restriction site within the $Cm^r$ gene. The pGB 301 plasmid DNA was cleaved by the restriction enzyme Bst E II, and was blunt ended with DNA polymerase I.

At the same time, the pYEJ 001 plasmid containing the 3.0 kb fragment coding for the expression of α-1,3 glucanase II gene was treated with EcoRI restriction endonuclease and the 3.0 kb fragment was blunt ended with DNA polymerase I. The pGB 301 plasmid DNA fragment and the α-1,3 glucanase II gene DNA fragment were then mixed at a ratio of 1 μg to 1 μg, and their blunt ends were ligated with 100 units of T4 ligase to reform a plasmid. In the recombinant plasmid thus obtained, the $Cm^r$ gene is cleaved, but the inserted α-1,3 glucanase II gene is intact and should achieve phenotypic expression.

Accordingly, the *S. sanguis Challis* strain was transformed by insertion of the modified pGB 301 plasmid containing the 3.0 kb fragment bearing the α-1,3 glucanase II gene. The transformation was carried out in accordance with the procedures of Le Blanc & Hassell [*J. of Bacteriol.,* 128(1), 347–355 (1976)] and Macrina et al. [Infec. & Imm., 28(3), 692–699 (1980)]. Colonies of the *S. sanguis Challis* strain which received the pGB 301 plasmid containing the α-1,3 glucanase II gene were cultured on the Brain Heart Infusion (B.H.I.) agar plates (Difco Laboratories) containing erythromycin (50 μg/ml). Each of these colonies was transferred to a B. H. I. agar plate containing chloramphenicol (10 μg/ml) to examine for the presence of $Cm^s$ (chloramphenicol-sensitive) colonies. Most of the *S. sanguis Challis* colonies showing chloramphenicol sensitivity were expected to have the α-1,3 glucanase II gene inserted into the pGB 301 plasmid.

Even for those *S. sanguis Challis* strains showing chloramphenicol sensitivity, phenotypic expression of the inserted α-1,3 glucanase II gene was observed in only about one third of the transformed colonies. This is because the gene fragment can be inserted in two different orientations. Expression of the gene product was tested for by transfer of the $Cm^s$ bacterium colonies by a sterilized stick to B. H. I. agar plates containing insoluble glucan. Because *S. sanguis* is a gram-positive bacterium it would be expected to secrete any α-1,3 glucanase II that it would produce. Expression and secretion of the α-1,3 glucanase II was detected by the presence of halos on the glucan plate. The α-1,3 glucanase II gene was thus successfully introduced into the cells of *S. sanguis,* a bacterium which is normally present in the oral cavity, and the phenotypic expression of the gene was achieved in that host.

EXAMPLE 7

In this example, the gene coding for the expression of the α-1,3 glucanase II gene was introduced into *S. sanguis* using plasmid pMN-1. While plasmid pGB 301 (FIG. 3) has two stable drug-resistant markers, $Em^r$ (erythromycin resistance) and $Cm^r$ (chloramphenicol resistance), and is a relatively small plasmid, there are several limitations on its efficient use. First, the copy number of pGB 301 in a *S. sanguis* cell is only about ten. Second, as a result of the low copy number, it is rather inefficient to culture small quantities of *S. sanguis* having plasmid pGB 301 and to make checks of the plasmid size or to culture large quantities of transformed *S. sanguis* and obtain the plasmid DNA.

As a result of these limitations, it was decided to combine pGB 301 and *E. coli* plasmid pUC 9 in order to make up an improved transformation system. Plasmid pUC 9 (Pharmacia, Uppsala, Sweden) is one of the smallest plasmids of *E. coli*, has a high copy number and have several polycloning sites. The pGB 301 plasmid was opened by cleavage at a unique *HaeIII* restriction site and pUC 9 was opened by cleavage at a unique SmaI site to produce, in both cases, linear molecules having blunt ends on both ends. The DNA fragments were then mixed and ligated by application of T4 DNA ligase to produce recombinant plasmids.

Figure 4:
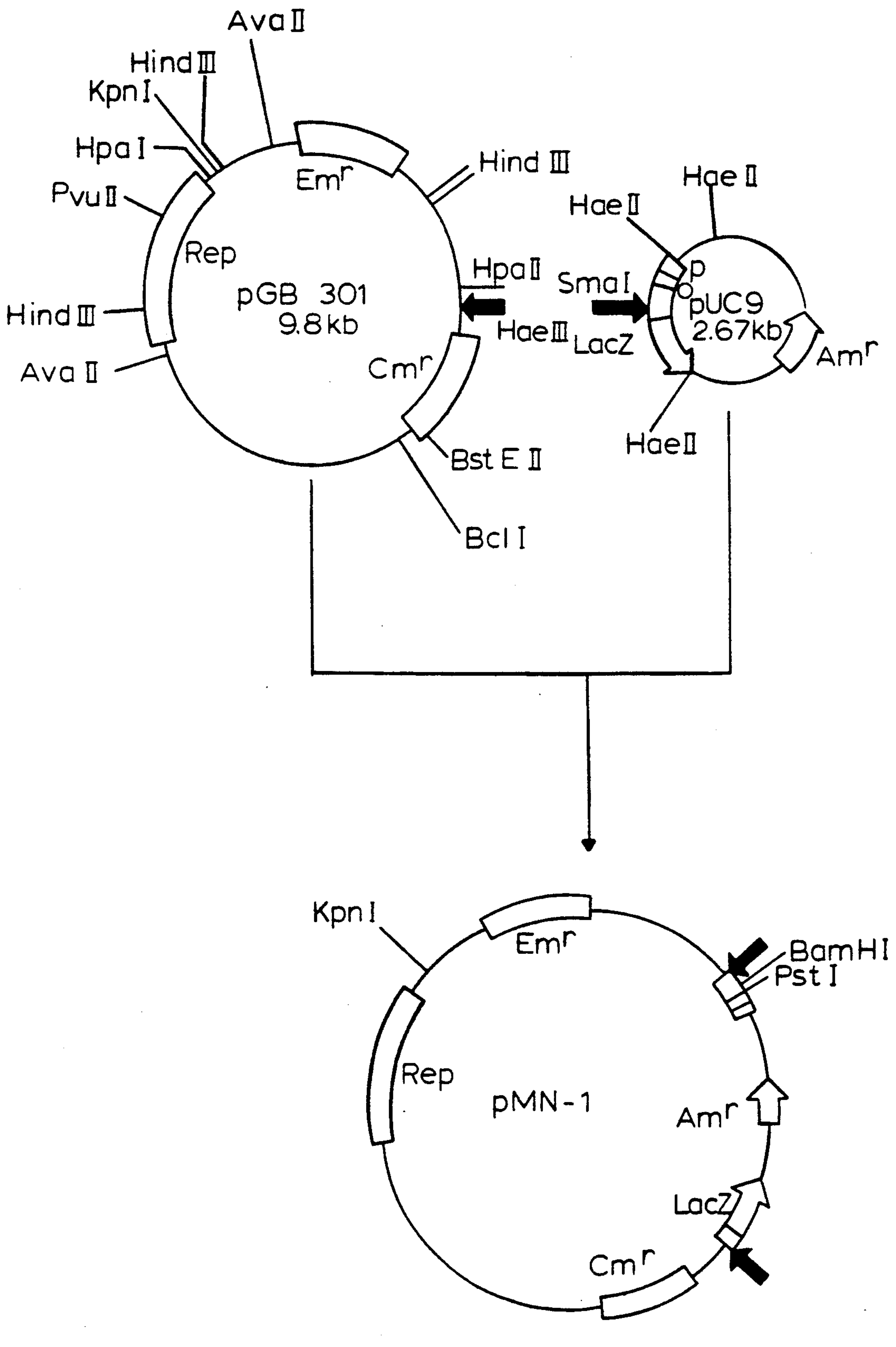
FIG. 4 is a diagramatic representation of the preparation of the *E.coli-S. sanguis* shuttle vector pMN-1.

The resulting plasmids were transformed into *E. coli* strain JM 103 (Pl−. *Isolation of the transformants was performed on an LB-plate containing* 50 μg/ml ampicillin, 1 mM IPTG (isopropyl-β-D-thiogalactopyranoside) and 0.1 mM X-Gal (5-Bromo-4-chloro-3-indolyl-β-D-galactoside). Tranformants having the recombinant plasmids grew well and formed white colonies. These colonies were isolated and plasmids were extracted therefrom. The size of these plasmids were analyzed and one of them having the size of 12 kb, was named pMN-1. The structure of pMN-1 is illustrated in FIG. 4. The size of pMN-1 was equivalent to the sum of that of pGB301 and pUC 9. The pMN-1 was used in following experiments as a cloning vector for the α-1,3 glucanase II gene.

This plasmid was also used as a shuttle vector to transform *S. sanguis* as described above, conferring resistance to ampicillin as well as to chloramphenicol and erythromycin in transformed *S. sanguis.*

It was previously noted that the α-1,3 glucanase II gene was inserted downstream of the synthetic promoter of the pYEJ 001 plasmid. Surprisingly, the expressed activity was not as strong as was expected. It was then suspected that the α-1,3 glucanase II gene was inserted counter to the regular direction relative to the synthetic promoter and expression was in fact regulated by an endogenous Bacillus promoter present on the EcoRI fragment. Accordingly, an experiment was conducted to determine the direction of insertion of the α-1,3 glucanase II gene.

Figure 5:
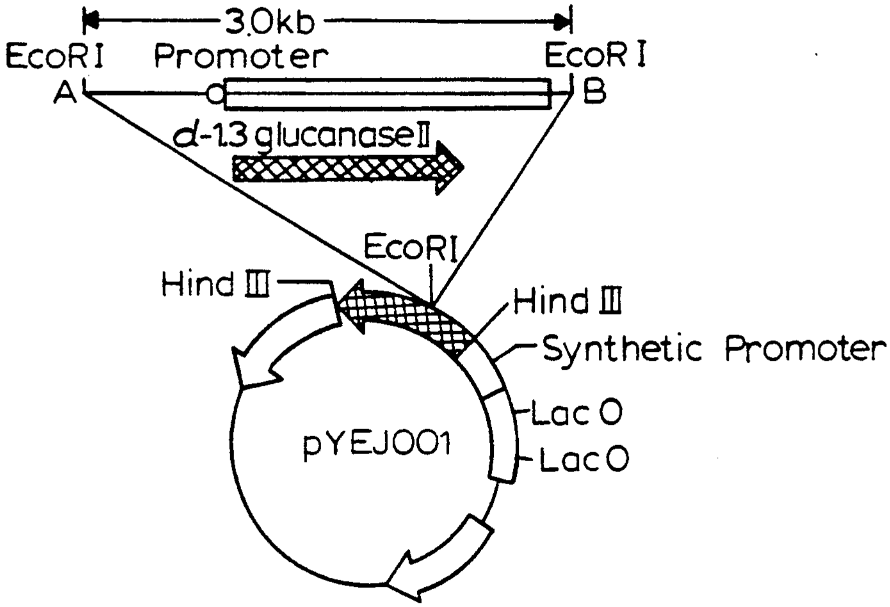
FIG. 5 is a diagramatic representation of properties of the α-1,3 glucanase gene cloned in the pYEJ 001.

The α-1,3 glucanase II gene inserted into plasmid pYEJ 001 (see FIG. 5) may be transcribed *in vitro* by the RNA polymerase of *E. coli.* More than twenty cultures which contained a 3.0 kb fragment cloned to the EcoRI site of plasmid pYEJ 001 were evaluated and on the basis of the cleaving distance from the PvuII restriction endonuclease site, it was concluded that in all cases the α-1,3 glucanase II gene was present in the reverse orientation and mRNA transcription progresses from A to B.

Statistically, in approximately one half of the cases, the α-1,3 glucanase II gene should have been inserted in the regular direction relative to the synthetic promoter, that is preceding B to A. In this configuration, a powerful phenotypic expression would have been expected and large quantities of α-1,3 glucanase II would be expected to be produced. Judging from the fact that no such strains were isolated it appears that the signal peptide of the α-1,3 glucanase II gene product of bacterium BC-8 was not cut away by the signal peptidase of *E. coli.* Further it appears that if the production of α-1,3 glucanase II under the control of the powerful synthetic promoter is excessive, the host bacteria accumulating α-1,3 glucanase II in the cells will die.

In those cases where the α-1,3 glucanase II gene was inserted in the reverse direction, that is A to B transcription by the regular promoter of the α-1,3 glucanase II gene of the bacterium BC-8 will take place. The transcription seems to be reduced to a very low level by the powerful competitive effect of transcription by the synthetic promoter. This appears to be confirmed by experiments in which when the α-1,3 glucanase II gene was inserted, under non-inductive conditions, downstream of promoters of strong inductive systems, such as the tryptophan promoter (Ptrp) or lactose promoter (Plac) of *E. coli.* In these cases products of genes inserted in both regular and reverse directions were obtained. The genes inserted in the regular direction exhibited considerably stronger production of α-1,3 glucanase II.

This observation suggests that in order to efficiently produce the α-1,3 glucanase II, the secretion signal peptide portion of the α-1,3 glucanase II gene product should be modified such that the signal peptide may be readily cleaved off of the α-1,3 glucanase II enzyme and the α-1,3 glucanase II gene should be inserted in the "regular" direction downstream of a strong promoter.

EXAMPLE 8

This example provides procedures for construction of plasmids coding for fusion proteins comprising the secretion signal peptide sequence of β-lactamase and the "mature", signal-free polypeptide product of the α-1,3 glucanase II gene. It has been found that β-lactamase, a product of the ampicillin resistance ($Am^r$) gene, is expressed effectively in *E. coli* as well as in *S. sanguis.*

Plasmid pMN-1 is manipulated to include the α-1,3 glucanase II gene in a similar manner to that used with pGB 301. That is, pMN-1 is cut with BstEII restriction endonuclease and blunt ended. At the same time, plasmid pYEJ 001 is cut with EcoRI restriction endonuclease to remove the 3.0 kb α-1,3 glucanase II gene fragment which is blunt ended. This fragment is then ligated to the linear pMN-1 fragment using T4 DNA ligase.

A gene fragment comprising the promoter and secretion signal peptide of β-lactamase is cleaved from plasmid pGH 54 modified by Ohgai et al., Annual Meeting of Japanese Molecular Biology Assn., Tokyo, Japan, Dec. 4, 1985, and is inserted into a NurI site within the DNA encoding the α-1,3 glucanase II gene on pMN-1 into which the gene has been inserted.

Figure 6A:
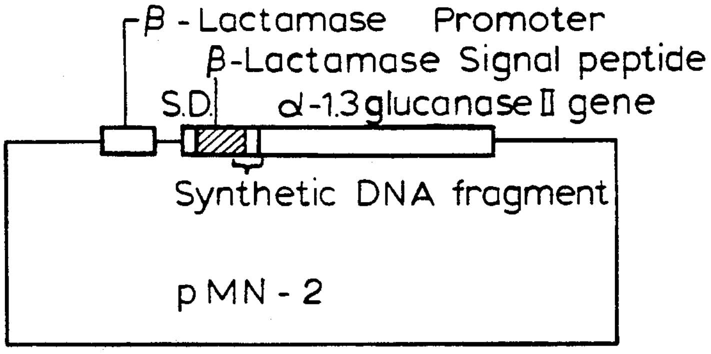
FIG. 6(*a*) is a diagramatic representation of the preparation of expression plasmid pMN-2.

The NurI site has been found to exist in the region of the α-1,3 glucanase II gene coding for the amino terminal of the enzyme polypeptide. In order to complete this construction, it is necessary to employ a synthetic linker serving to connect the β-lactamase signal peptide encoding DNA on the pGH 54 fragment to the remainder of the α-1,3 glucanase II gene (3' to the NurI site) and build up the DNA (5' to the NurI site) encoding the amino terminal of the enzyme. The resulting plasmid (designated pMN-2) is schematically represented in FIG. 6*a*.

The promoter and signal sequence of the β-lactamase gene incorporated in the plasmid are as set out below. The promoter sequence is underscored and the ribosome binding site is doubly underscored.

TGGTTTCTTA GACGTCAGGT GGCACTTTTC GGGGAAATGT GCGCGGAACC

CCTATTTGTT TATTTTTCTA AATACATTCA AATATGTATC CGCTCATGAG

ACAATAACCC TGATAAATGC TTCAATAATA TTGAAAAAGG AAGAGT

| | | | | | | | | | | | | |
|---|---|---|---|---|---|---|---|---|---|---|---|---|
| ATG | AGT | ATT | CAA | CAT | TTC | CGT | GTC | GCC | CTT | ATT | CCC | TTT |
| Met | Ser | Ile | Gln | His | Phe | Arg | Val | Ala | Leu | Ile | Pro | Phe |
| TTT | GCG | GCC | TTT | TGC | CTT | CCT | GTC | TTC | GCG | | | |
| Phe | Ala | Ala | Phe | Cys | Leu | Pro | Val | Phe | Ala | | | |

EXAMPLE 9

Figure 6B:
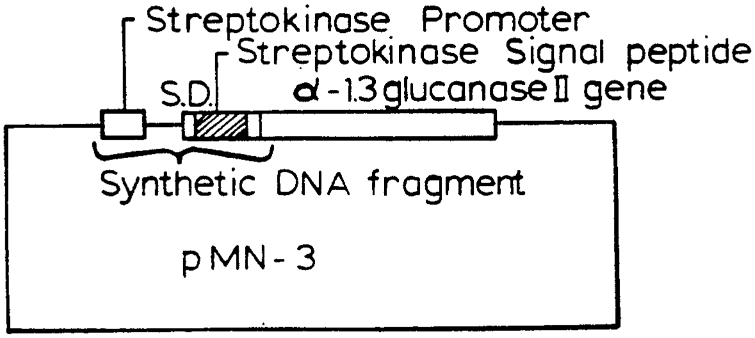

In this example plasmids are constructed coding for the expression of a fusion protein comprising the secretion signal peptide for streptokinase and the "mature", signal-free polypeptide product of the α-1,3 glucanase II gene. A gene fragment comprising the promoter and secretion signal peptide for streptokinase was cloned from *Streptococcus equicimilis* and its base sequence was determined (Malke & Ferretti, Proc. Natl. Acad. Sci. U.S.A., 81, 3557-3561 (1984); Malke et al., Gene, 34, 357-362 (1985). This gene sequence is known to code for the secretion of streptokinase by cells of *S. equicimilis* as well as by *E. coli.* Plasmid pMN-3 (see FIG. 6*b*) is obtained by synthesizing a DNA sequence corresponding to the promoter and signal peptide of this enzyme together with the α-1,3 glucanase II gene region 5' to the NurI site and ligating the synthesized DNA sequence into the NurI site in a pMN-1 plasmid manipulated to include the gene coding for the α-1,3 glucanase II protein.

The promoter and signal sequence of the streptokinase gene incorporated in the plasmid are as set out below. The promoter sequence is underscored and the ribosome binding sequence is doubly underscored.

TATCATTTTA AAAAAATCAT TAGGTTTTTA TTTGTGTCTT TAAAACCATT

ATGTTATTCT AATAATGGGG ATTGAAACTT AACTTTTAGG AGGTTTCT

| | | | | | | | | | | | | |
|---|---|---|---|---|---|---|---|---|---|---|---|---|
| ATG | AAA | AAT | TAC | TTA | TCT | TTT | GGG | ATG | TTT | GCA | CTG | CTG | TTT |
| Met | Lys | Asn | Tyr | Leu | Ser | Phe | Gly | Met | Phe | Ala | Leu | Leu | Phe |

-continued

| | | | | | | | | | | | | | |
|---|---|---|---|---|---|---|---|---|---|---|---|---|---|
| GCA | CTA | ACA | TTT | GGA | ACA | GTC | AAT | TCT | GTC | CAA | GCT | ATT | GCT |
| Ala | Leu | Thr | Phe | Gly | Thr | Val | Asn | Ser | Val | Gln | Ala | Ile | Ala |

Cultures of *E. coli* strain JM 103 and *S. sanguis* may be transformed according to the methods disclosed above with plasmids pMN-2 and pMN-3 and are expected to express both erythromycin and ampicillin resistance. The transformed cells are expected to have a considerable quantity of α-1,3 glucanase II accumulated in their periplasm and the transformed *S. sanguis* cells are expected to secrete the enzyme.

In this way, phenotypic expression of the α-1,3 glucanase II gene is expected to be successfully demonstrated in *S. sanguis* which is a bacterium indigeneous to the oral cavity. As previously disclosed, insertion of the α-1,3 glucanase II gene in the regular direction relative to the promoter, and replacement of the signal peptide with one that functions in the cells of *S. sanguis* are important to the expression and secretion of large quantities of α-1,3 glucanase II.

*E. coli* and *Streptococcus sanguis* transformed with plasmids pMN-1, pMN-2 and pMN-3 were plated out on a medium containing Todd Hewitt broth agar supplemented with 0.2% α-1,3-D-glucan and the relative degree of halo production (representing α-1,3 glucanase II production) was determined as set out in Table 1 below:

TABLE 1

| Plasmid | *E. coli* Host | *S. sanguis* Host |
|---|---|---|
| pMn-1 | − | − |
| pMN-2 | + | ± |
| pMN-3 | ++ | + |

The effect on elimination of insoluble glucan in the in vitro procedure described below with respect to dextranase testing was determined for *S. sanguis* alone and *S. sanguis* respectively transformed with pMN-1, pMN-2 and pMN-3. The results are set out in Table 2 below.

TABLE 2

| | | Plasmid Harbored | | |
|---|---|---|---|---|
| | None | pMN-1 | pMN-2 | pMN-3 |
| % Insoluble glucan remaining | 100 | 99 | 46 | 24 |
| % Elimination Efficiency | 0 | 1 | 54 | 76 |

*Streptococcus mutans* microorganisms and *Streptococcus sanguis* microorganisms with plasmid pMN-2 or pMN-3 were jointly inoculated into sterilized test tubes containing either Todd Hewitt Broth (Difco) or Brain Heart Infusion medium (Difco) containing 2% sucrose. Following shaking culture overnight at 37° C., no insoluble glucan formation was found at the bottom of the tube, signifying utility of recombinant glucanase products of the present invention in inhibiting glucan formation.

EXAMPLE 10

This example related to the dextranase producing CB-8 cells and more particularly to general procedures for growth of cells in culture; general procedures for harvesting of enzyme from the culture medium; two specific procedures for production of dextranase enzyme from CB-8; and characterization of physiocochemical and enzymatic properties of the enzyme.

A. General Considerations Relating to Cultured Growth of CB-8

(1) Culture Medium

For producing dextranase, CB-8 can be cultured using any suitable natural or a synthetic medium. For industrial production, however, it is more advantageous in terms of cost to use jar fermenter culture with a liquid medium.

Nutrients of the medium may be those commonly used for microorganisms. For instance, nitrogen sources include ammonium phosphate, ammonium sulfate, peptone, and yeast extract. Inorganic salts include salts of phosphoric acid, sodium, potassium, magnesium, and calcium. Addition of dextran or insoluble glucan produced by *Streptococcus mutans* is effective as a carbon source and an inducer for dextranase production.

(2) Growth Conditions

The CB-8 organism is typically inoculated on the medium prepared according to (1) above, and the bacterium is allowed to grow at the specified culture temperature, preferably within the range from 30° C. to 37° C., with pH of the medium in the range from 6 to 7, for a period of time allowing dextranase production to be optimized. The incubation period depends on the culture conditions, but generally from 24 to 48 hours are needed in the case of jar fermenter culture systems.

B. Harvest and Purification of Dextranase From Culture

The liquid culture in which dextranase has been produced is typically centrifuged to remove bacterial cells and provide a crude enzyme solution.

The crude enzyme solution thus obtained is fully usable as a product without any further processing. It is possible, however, to obtain a further purified enzyme solution of dextranase by applying, singly or in combination, various known purification processes, such as ultrafiltration, vacuum concentration, salting out with ammonium sulfate, solvent fractionation with ethanol, or acetone, isoelectric precipitation, and column chromatography techniques.

C. Methods for the Production of Dextranase Using Arthrobacter sp. CB-8

(1) Procedure No 1.

Liquid medium for the production of dextranase was prepared by adding 0.5%, 1.0%, 2.0% or 3.0% of dextran (Wako Junyaku; molecular weight: 60,000~90,000) to a liquid medium (pH 7.0) containing 0.5% of bactotryptone (Difco), 0.2% of yeast extract (Difco), 0.1% of potassium phosphate, and 0.1% of sodium chloride. 100 ml of each liquid medium was put into 500-ml Erlenmeyer flasks with a cotton plugs. After sterilization, 1 ml of a separately sterilized 1 M magnesium sulfate aqueous solution and 1 ml of a separately sterilized 0.1 M calcium chloride aqueous solution were added to the flask. 4 ml of a CB-8 culture, which had been precultured for 24 hours on a medium containing 0.5% of dextran and above-mentioned components, was inoculated to the flasks. The inoculated medium was incubated at 37° C. on a rotary shaker. Medium was sampled out at the various culture times and assayed for dextranase activity. As shown in Table 4, when the dextran concentration was 0.5%, highest dextranase activity was obtained at 24 hours culture. When the dextran concentration was 2.0%, highest activity was observed at 48 hours culture.

TABLE 4

Effect of the Concentration of Dextran in Culture Medium and Culture Time on Dextranase Production (Unit/ml)

| Concentration of dextran in culture medium (%) | Culture time (hr) | | | | |
|---|---|---|---|---|---|
| | 0 | 12 | 24 | 48 | 58 |
| 0.5 | — | 0.08 | 0.20 | 0.09 | 0.04 |
| 1.0 | — | 0.08 | 0.13 | 0.15 | 0.05 |
| 2.0 | — | 0.04 | 0.17 | 0.32 | 0.32 |
| 3.0 | — | 0.05 | 0.19 | 0.32 | 0.28 |

(2) Procedure No. 2

500 ml of a liquid medium (pH 7.0), which contained 0.5% of bactotryptone, 0.2% of yeast extract, 0.1% of potassium phosphate, 0.1% of sodium chloride, and 1.0% of dextran, was prepared in a 3-l Erlenmeyer flask with a cotton plug. After sterilization, 5 ml of a separately sterilized 1 M magnesium sulfate aqueous solution and 5 ml of a separately sterilized 0.1 M calcium chloride aqueous solution were added to that flask.

20 ml of a CB-8 culture which had been grown on the same medium for 24 hours was inoculated on the medium prepared above. The inoculated medium was incubated at 37° C. by the rotary type shaking culture for 24 to 48 hours. A total of 18 l of the culture medium was prepared by cultivation at this scale. After cultivation, the liquid culture was collected and centrifuged to obtain the supernatant. The supernatant was concentrated by ultrafiltration, and then subjected to salting-out by adding ammonium sulfate to 80% saturation. After salting-out, the precipitate was collected by centrifugation, dissolved in a small amount of 50 mM phosphate buffer (pH 6.5) and dialyzed against the same buffer.

The dialyzed solution was applied to a DEAE-Sephacel column (Pharmacia) equilibrated with the same buffer and eluted by linear gradient of 0 to 0.5 M sodium chloride solution (50 mM phosphate buffer, pH 6.5). The eluate was then subjected to gel filtration with a Bio-Gel P-30 (BIO-RAD) column equilibrated with 50 mM phosphate buffer (pH 6.5). The fractions containing dextranase activities were collected, and subjected to crystalization with ammonium sulfate for three times. After these treatments, purified dextranase preparation was subjected to SDS-polyacrylamide gel electrophoresis, and a single protein band was observed. This establishes that, with the abovementioned purification procedure, dextranase was purified to an electrophoretically pure level.

The results of the above-mentioned purification procedure are shown in Table 5. A yield of 368 units, 4.6 mg of purified dextanase, was obtained from 18 l of the culture supernatant, and its specific activity was 80.0 (unit/mg protein).

TABLE 5

Enzymatic Activity, Yield and Specific Activity In Each Step of CB-8 Dextranase Purification

| | Volume (ml) | Total dextranase activity (unit) | Total protein (mg) | Specific activity (unit/mg protein) | Yield (%) |
|---|---|---|---|---|---|
| Culture supernatant | 18,000 | 4,860 | 633 | 7.7 | 100 |
| Salting out with ammonium sulfate | 61 | 4,209 | 518 | 8.1 | 86.6 |
| DEAE-Sephacel ion-exchange chromatography | 34 | 2,448 | 41 | 59.7 | 50.3 |
| Bio-gel P-30 gel filtration | 19 | 1,957 | 31 | 63.1 | 40.3 |
| Crystallyzation | 4 | 368 | 4.6 | 80.0 | 7.6 |

D. Physicochemical and Enzymatic Properties of Dextranase

Dextranase obtained by the above-mentioned production methods has the following physiochemical and enzymatic properties.

(1) Molecular Weight

The molecular weight of the dextranase as determined by SDS-polyacrylamide gel electrophorese is about 62,000. Molecular weight determination by gel filtration (Pharmacia, Superose 12) was about 40,000.

(2) Method for Measuring the Activity 0.1 ml of the enzyme solution is added to 0.9 ml of 50 mM phosphate buffer, pH 6.5, containing 0.555% dextran (molecular weight: 10,000~20,000), and the mixture is incubated at 37° C. for 30 minutes. After the reaction is stopped, the amount of reducing sugar produced is measured by Somogyi-Nelson method. The enzymatic activity which increases a reducing power equivalent to 1 $\mu$ mole of glucose per 1 minute was defined as one unit.

(3) Optimum pH and Stable pH

Figure 12:
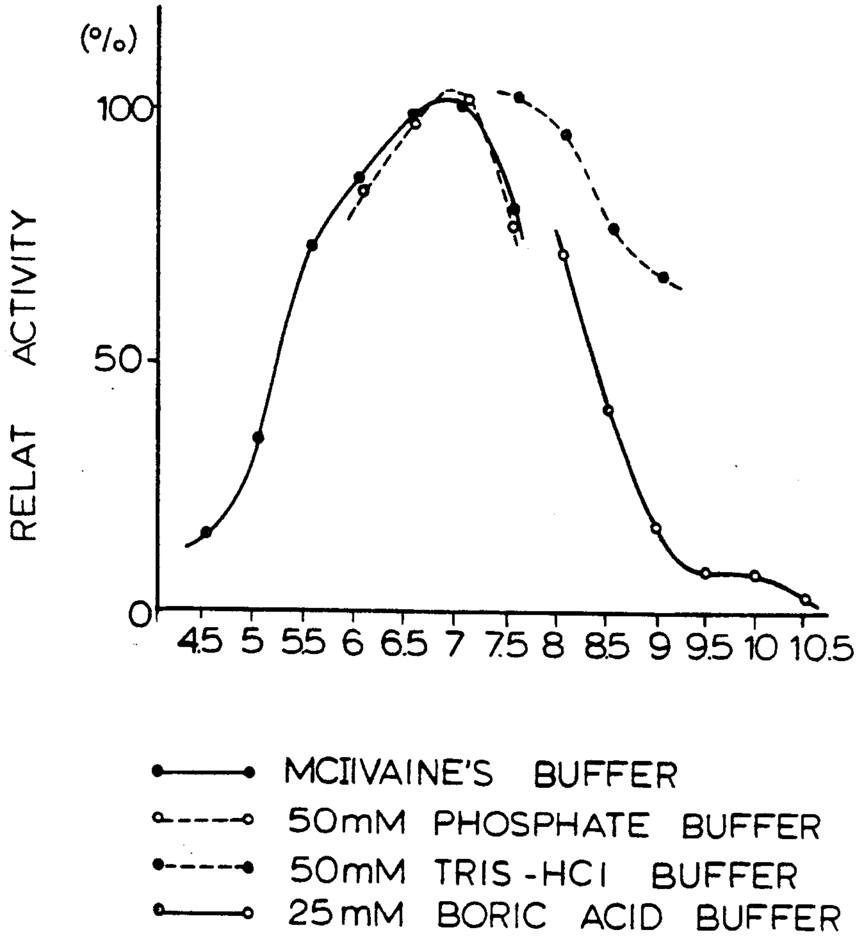
FIGS. 12 through 15 are graphic representations of results of testing enzymatic properties of dextranase.

FIG. 12 shows the activity of the dextranase under various pH conditions. The functional pH range for the dextranase reaction on dextran is from pH 5.5 to 7.5, and in particular, the dextranase exhibits high activity at the range of pH 6.5 to 7.0.

Figure 13:
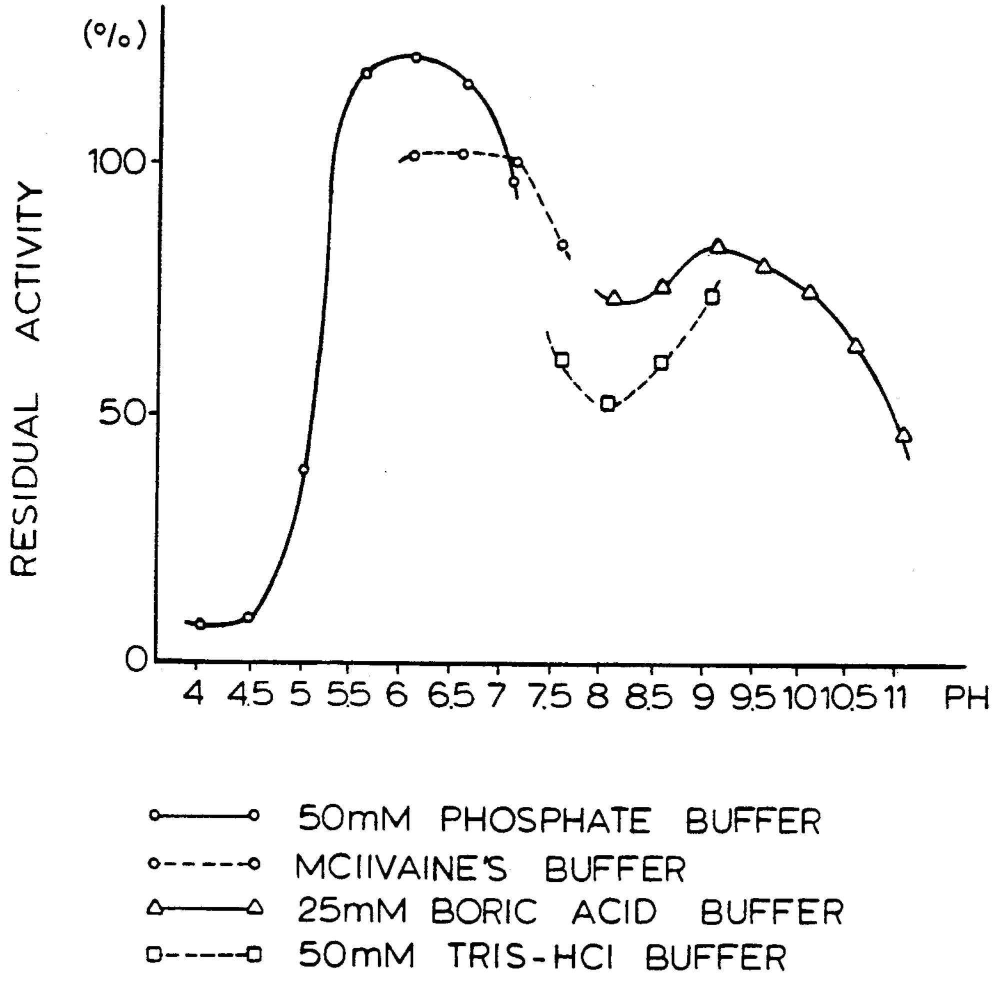

FIG. 13 shows the stability of the dextranase under various pH conditions based on residual activity levels measured after keeping dextranase at 37° C. for one hour under those pH conditions. The graph indicates that dextranase is quite stable at the range of pH 5.5 to 7.0.

(4) Optimum Temperature and Stable Temperature

Figure 14:
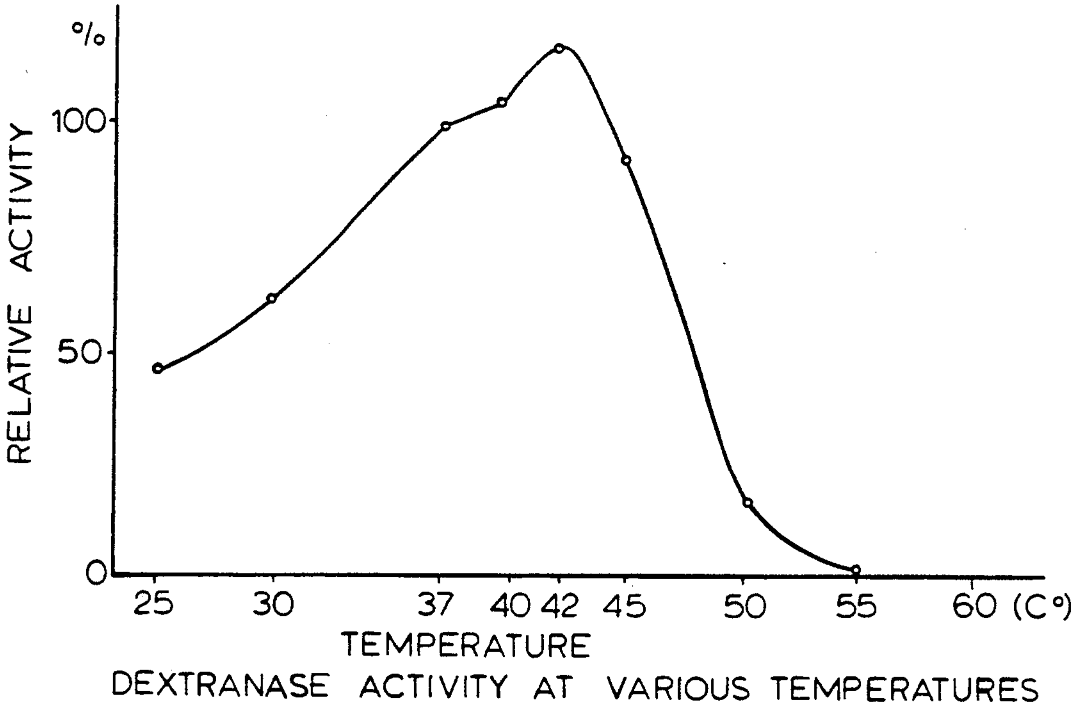
Figure 15:
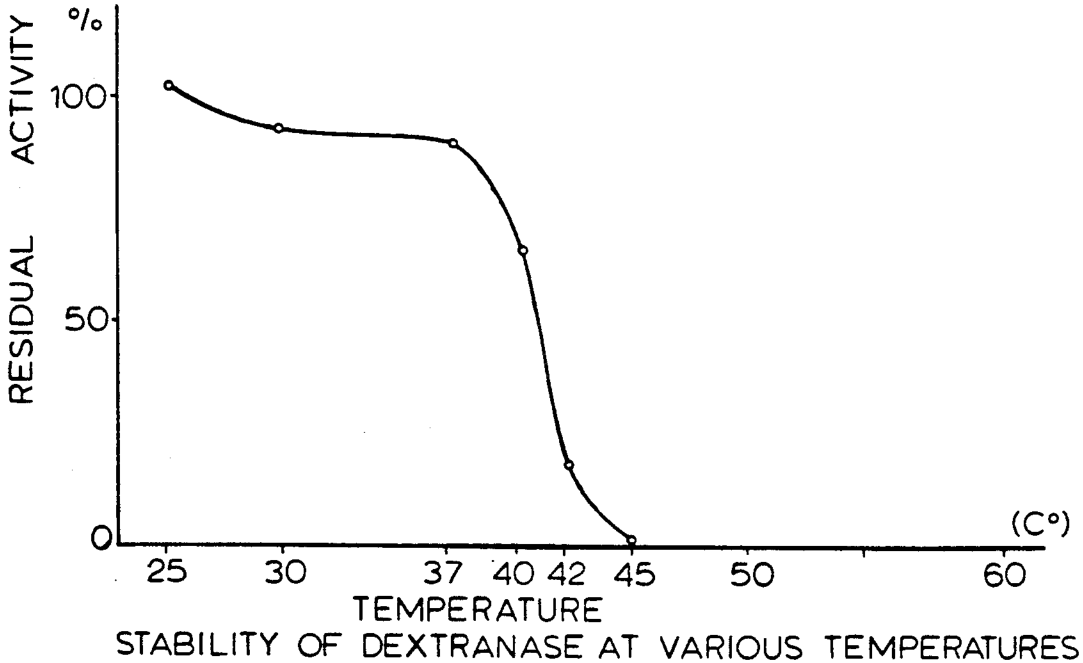

The optimum temperature for the reaction of dextranase activity on a dextran substance is, as shown in FIG. 14, 42° C. FIG. 15 shows the stability of dextranase at various temperatures based on the residual activity levels measured after keeping dextranase at pH 6.5 and at the indicated temperatures for one hour. As indicated, dextranase is relatively stable below 37° C.

(5) Effects of Metallic Ions and Enzyme Inhibitors

As shown in Table 6 below, dextranase was significantly inhibited by $Ag^{2+}$, $Cu^{2+}$, and $Hg^{2+}$, and it was also inhibited strongly by pCMB (p-chloromercuribenzoic acid).

TABLE 6

Effects of Metallic Ions and Enzyme Inhibitors on Dextranase Activity

| Metallic ion or inhibitor | Concentration (mM) | Relative activity (%) |
|---|---|---|
| None | — | 100 |
| NaCl | 10 | 100 |
| KCl | 10 | 113 |
| $CaCl_2$ | 1 | 113 |
| $MgSO_4$ | 1 | 113 |
| $FeCl_2$ | 1 | 115 |
| $PbCl_2$ | 1 | 103 |
| $CaCl_2$ | 1 | 81 |
| $MnCl_2$ | 1 | 77 |
| $ZnCl_2$ | 1 | 77 |
| $CuSO_4$ | 0.1 | 7 |
| $AgNO_3$ | 0.1 | 0 |
| $HgCl_2$ | 0.1 | 0 |
| $FeCl_3$ | 1 | 104 |
| EDTA | 1 | 122 |
| o-Phenanthroline | 1 | 100 |
| pCMB | 1 | 29 |

(6) Isoelectric Point

The isoelectric point (pI) of dextranase was determined to be 4.0 by using the polyacrylamide gel isoelectrofocusing.

(7) Amino Acid Sequence

Purified dextranase was subjected to N-terminal amino acid sequence analysis. The N-terminal amino acid sequence for the first 12 residues of dextranase produced by CB-8 was found to be as follows:

Glu—Arg—Ala—Ile—Thr—Thr—Val—Asp—Asn—Gly—Asn—Leu
1 2 3 4 5 6 7 8 9 10 11 12

EXAMPLE 11

This example relates to the cloning and manipulation of the CB-8 gene encoding dextranase.

CB-8 was inoculated to LB-broth including 1% glucose and was cultured overnight. The cultured cells were collected by centrifugation, washed with distilled water and suspended in 0.02M tris-HCl (pH8.2) buffer. Polyethylene glycol 4000 was added to this suspension to 12% (w/v), lysozyme (Egg white) was then added to a concentration of lmg/ml and the reaction mixture was incubated for one hour at 37° C. After incubation, the mixture was centrifuged and the precipitate was suspended in 0.01M tris-HCl (pH8.2) buffer. Pronase E was added to a concentration of 1 mg/ml along with SDS solution (pH8.2) to a concentration of 1% and this was incubated for 30 minutes at 37° C. This suspension was then subjected to phenol extraction and ethanol precipitation was carried out on the aqueous phase. Precipitated CB-8 genomic DNA was collected by glass-stick and was dissolved into 0.01M tris-HCl (pH8.0) buffer containing 1 mM EDTA. The genomic DNA was further purified by ultra-centrifugation with CsCl. By the above described procedures, 441 μg of purified genomic DNA was obtained from 300 ml of culture broth of CB-8.

Purified CB-8 genomic DNA was subjected to partial digestion by Sau 3A-1 and the digest was subjected to agarose gel electrophoresis. DNA corresponding in length to 4.3 kb-9.4 kb was recovered from that gel by electroelution. These DNAs were ligated to the BamHI site of pUC 19 by T4 DNA ligase and cloned into *E. coli* HB 101 cells. By the above described procedures, a CB-8 genomic DNA library consisting of about 10000 cells was obtained from 500 ng of the genomic DNA having a length of 4.3 kb-9.4 kb.

Transformed cells from CB-8 genomic DNA library were plated onto LB-plates (about 500 cells per plate) containing 0.2% blue dextran, 0.8% dextran and 50 μg/ml ampicillin and cultured for 24-50 hours at 37° C. Thereafter, colonies which produced a colorless and transparent halo around them as a result degradation of blue dextran by dextranase activity were selected. By this procedure, three positive clones which had acquired the ability to produce dextranase were obtained from about 10000 transformed cells.

Figure 16:
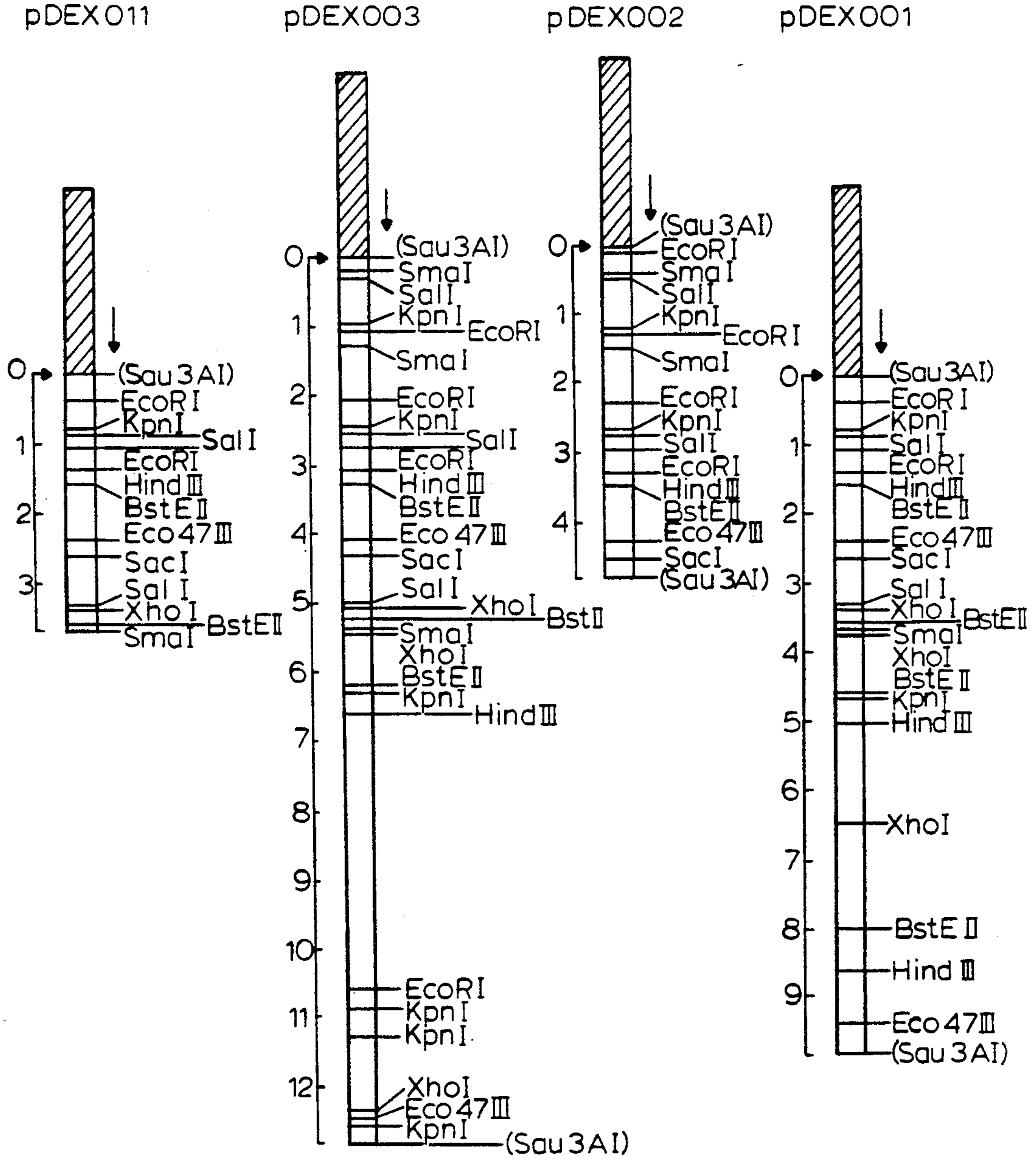
FIGS. 16 and 17 provide restriction maps of cloned DNA of the invention.

The three dextranase producing transformant were inoculated into TB-medium (Terrific broth) and cultured for 16 hours at 37° C. Thereafter each culture broth was centrifuged. From precipitated cells, plasmid DNA was extracted by alkaline lysis method [Birnoboim et al., *Nucleic Acid Res.*, 7, 1513 (1979)] and further purified by ultra-centrifugation with CsCl. Size analysis performed on the plasmid DNAs revealed sizes of 12.5 kb, 7.5 kb and 15.5 kb and the plasmids were named, pDEX001, pDEX002 and pDEX003, respectively. Restriction maps were made for each plasmid DNA and the results were shown in FIG. 16. In these restriction maps white portions indicate the DNA region derived from CB-8 and black portions those derived from pUC19. Black triangles indicate the multicloning site from pUC19 and arrows indicate the transcriptional direction of β-galactosidase gene coded by the native pUC19 plasmid.

In the insert of these three plasmids there existed regions displaying restriction map homology. Based on the assumption that dextranase was coded in these regions, plasmid pDEX011 was developed from pDEX001. pDEX011 contained the homologous region, but was smaller in length than pDEX001. The plasmid was used to transform *E. coli* HB101 cells, with the result that the transformants also produced dextranase.

Upon finding that active dextranase was produced in *E. coli* into which CB-8 dextranase gene had been cloned, the amount of its production, place of accumulation, and possibility of induction were examined. First, transformants (*E. coli* HB101) harboring plasmids pDEX001, and pDEX011, were inoculated to LB-broth containing 50 μg/ml of ampicillin, and subjected to shaking culture at 37° C. After 16 hours the culture was centrifuged, and the culture supernatant was dialyzed against 50 mM Na-phosphate buffer (pH 6.5). The bacterial cells were subjected to osmotic shock [Chan et al., *Proc. Nat'l. Acad. Sci. (USA)*, 78, 5401 (1981)] to extract protein which exists in the periplasmic fraction. After the osmotic shock, the bacterial cells were suspended in 1 ml of 50 mM Na-phosphate buffer (pH 6.5) and disrupted by sonication to allow extraction proteins of the cytoplasm fraction. Each of these extracts was dialyzed against the abovementioned buffer and the dextranase activity of each fraction was measured. The results are shown in Table 7. The amount of enzyme which increases reducing sugar equivalent to 1 μmol of glucose per minute under conditions of the activity measurement method was defined to be one unit. For periplasmic and cytoplasmic fractions, the activity is indicated based on the number of bacterial cells contained in 1 ml of liquid culture.

TABLE 7

Dextranase Activities of Culture Supernatant, Periplasmic and Cytoplasmic Fractions Derived from transformed *Escherichia coli* cells

| Fraction | Dextranase activity (unit/ml) | |
|---|---|---|
| | pDEX001 transformant | pDEX011 transformant |
| Culture supernatant | 0 | 0 |
| Periplasmic fraction | 0.00140 | 0.00590 |
| Cytoplasmic fraction | 0.00013 | 0.00006 |

As shown in Table 7, for both transformants the most significant dextranase activity was found to be in the periplasmic fraction. It was accordingly determined that dextranase produced in the cytoplasm of transformed *E. coli* cells was passed through the inner membrane, secreted and accumulated in the periplasm.

An attempt was made to determine whether, like CB-8, the production of dextranase by the transformed *E. coli* is induced when the medium contained dextran. A LB-broth containing 1% of dextran and 50 μg/ml of ampicillin was used as a culture medium for the pDEX001 and pDEX011 HB101 transformants. In experiments similar to those mentioned immediately above, the dextranase activity in the periplasmic fraction was measured and no increase in dextranase activity was observed. As the dextranase gene of CB-8 was inserted in the downstream of the Lac Z promoter of pUC19, there was a possibility that the induction could be caused by IPTG, an inducing substrate of Lac Z. Hence the transformants were cultured with a LB-broth containing 1 mM IPTG, and 50 μg/ml of ampicillin. Determination of dextranase activity of each periplasmic fraction again showed no increase in the dextranase activity.

On the basis of the above results, it was hypothesized that a natural dextranase promoter was involved in the transcription of the dextranase gene in the transformants and that the gene was constitutively transcribed in *Escherichia coli*, irrespective of the presence of dextran.

To confirm that the dextranase produced by the transformants is a product of the dextranase gene derived from CB-8, Western blot hybridization analysis was applied. First, proteins of the periplasmic and cytoplasmic fractions of the pDEX011 transformant were subjected to SDS-gel electrophoresis and migrated proteins were blotted on a filter. Anti-CB-8 dextranase rabbit serum was used as the primary antibody and alkaline phosphatase bound to anti-rabbit IgG goat IgG was used as the secondary antibody to detect dextranase on the filter based on alkaline phosphatase reaction. A substance detected by antigen-antibody reaction with anti-CB-8 dextranase serum was clearly present in both the periplasmic and cytoplasmic fractions of the pDEX011 transformant. The antibody stained bands of both fractions were found at the region of the slightly higher molecular weight than that of the native CB-8 dextranase. On the other hand, antigenically reactive substances were not found in *Escherichia coli* (HB-101) carrying no plasmid. On the basis of the above-mentioned results, the pDEX011 transformant was clearly shown to produce dextranase protein by using the information coded by the CB-8 dextranase gene.

DNA sequence analysis was carried out on the portion of pDEX011 where dextranase was considered to be coded.

Figure 17:
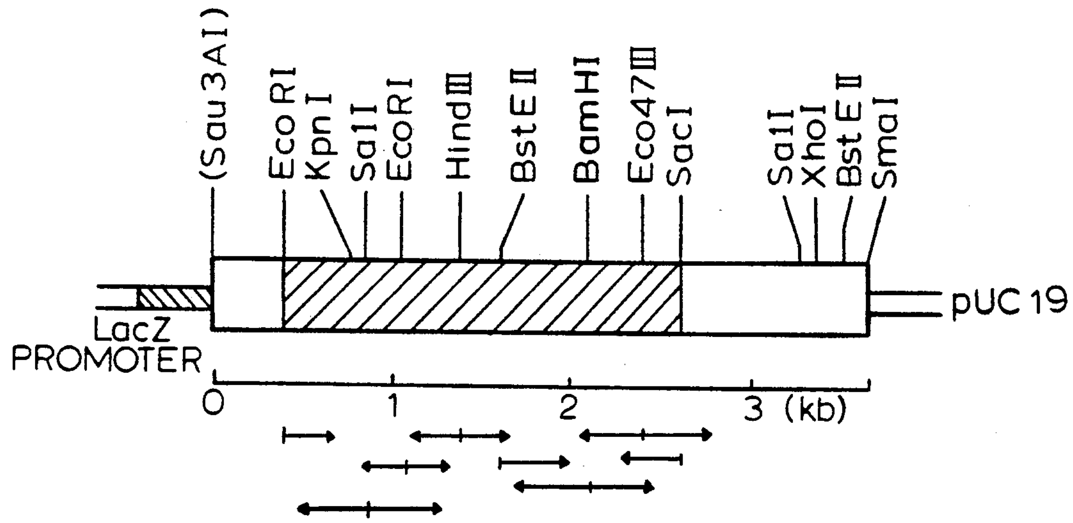

FIG. 17 shows a restriction enzyme map of the DNA portion derived from CB-8 DNA in pDEX011. The dark-shaded portion is the dextranase coding region estimated by the following techniques. pDEX011 was digested by various restriction enzyme and resulting DNA fragments were ligated to pUC19 and cloned into *Escherichia coli* HB101 cells to determine whether dextranase activity was produced or not. In this way, the smallest DNA region which coded active dextranase information was determined. The sequence analysis was made in the direction of arrows by the dideoxy sequencing method using M13 phage [Sanger et al., *Proc. Nat'l. Acad. Sci. (USA)*, 74, 5463 (1977)].

The nucleic acid sequence of the CB-8 dextranase gene determined by the above-mentioned experiment and the amino acid sequence deduced from it are shown in FIG. 18A to D. The dextranase gene of CB-8 has an open reading frame of 1920 base pairs. 6 base pairs upstream of the 5' terminal of the open reading frame, a sequence of GAGGAA was observed, which was considered to be a ribosome binding site (SD sequence). The total number of coded amino acids in the open reading frame is 640. And a sequence of 12 amino acid residues indicated by the double underlining in FIGS. 18A to D was identical to that previously identified as the N-terminal amino acid analysis of CB-8 dextranase. Upstream of this sequence, a sequence of 49 amino acid residues (underlined in FIGS. 18A to D) is considered to be the sequence of a signal peptide. The dextranase CB-8 is thus considered to be produced in the cells as a polypeptide chain consisting of 640 amino acid residues. At the time of secretion from the bacterial cells, the signal peptide portion consisting of 49 amino acid residues is believed to be cut off by signal peptidase, and the mature dextranase protein consisting of 591 amino acid residues is then accumulated in the periplasm. The molecular weight of the mature dextranase was calculated as 66644.22 based on the nucleic acid sequence analysis. This value agrees well with the molecular weight of 62000 estimated by the SDS polyacrylamide gel electrophoresis of the CB-8 dextranase protein.

EXAMPLE 12

This example relates to the development of transformed *Streptococcus sanguis* and other oral microorganisms capable of producing dextranase for the enzymatic removal of insoluble glucan of the dental plaque. For this purpose the dextranase gene originally cloned in coliplasmid pUC19 was introduced in *Streptococcus sanguis*. Few shuttle vector plasmids that are able to replicate in both *Escherichia coli* and *Streptococcus sanguis* are available. Plasmid pMNK was therefore constructed by the in vitro joining of the pUC18 or pUC19 derivative ($Amp^r$) and pVA749 ($Em^r$), part of plasmid pVA838 described by Macrina et al., Gene, 19, 345-353 (1982). These plasmids were principally used as shuttle vectors for the dextranase gene in place of pMN-1 which was used as the cloning vector of α-1,3 glucanase II gene.

Figure 19:
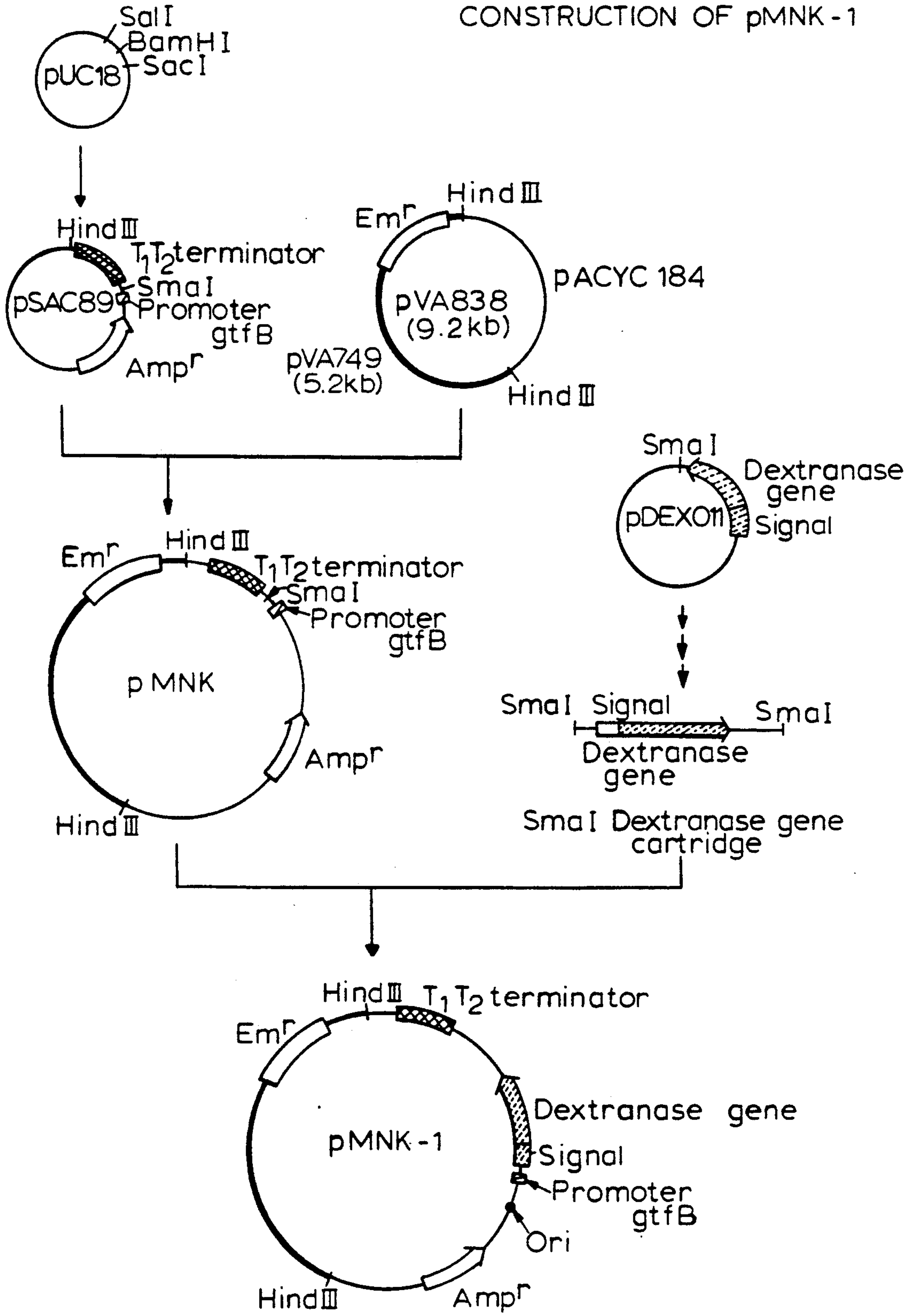
FIG. 19 is a diagramatic representation of constructions of expression plasmid pMNK-1.

A. Construction of plasmid pMNK and pMNK-1 (Cf. FIG. 19)

1) To allow strong and efficient expression of the dextranase gene in *Streptococcus sanguis*, the gtfB gene-promoter of *Streptococcus mutans* [Shiroza et al., *J. Bacteriol.,* 169(9), 4263–4270 (1987)] was used along with the rrn gene-terminator of *Escherichia coli.* A Dra I promoter fragment (84bp) of the gtfB gene was inserted into the Sac I site of pUC18 blunt-ended by the Kenow fragment of DNA polymerase I. The $T_1T_2$ fragment (0.8 kb) of rrn terminator described in Brosius et al., *J. Mol. Biol.,* 148, 107–127 (1981), derived from plasmid pKK 223-3 (Pharmacia LKB Biotechnology, AB) wherein it was present between SalI and BamHI linkers, was inserted as a BamHI-SalI fragment between the BamHI and SalI sites of partially modified polycloning site of pUC18 to provide plasmid pSAC89.

2) Plasmid pVA749 was obtained from plasmid pVA838 as a HindIII fragment (5.2 kb).

3) pSAC89 was cut at its HindIII site, ligated with the pVA749 HindIII fragment, and pMNK was thus obtained as a chimeric plasmid pVA749:PSAC89 by selection of $Amp^r$ (25 μg/ml), $Em^r$, (100 μg/ml) transformants of *Escherichia coli.* The resulting plasmid pMNK is a shuttle vector that is able to replicate in both *Escherichia coli* and *Streptococcus sanguis* and also is an expression vector that carries a strong streptococcal promoter upstream of SmaI cloning site.

Figure 20:
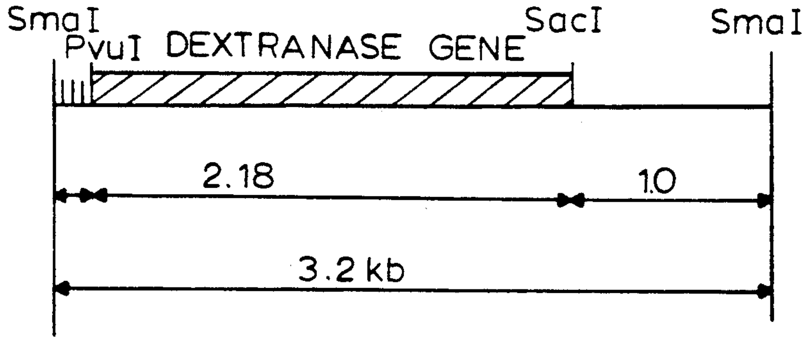
FIG. 20 is a diagramatic representation of an SmaI dextranase gene cartridge derived from plasmid pDEX011.

4) A dextranase gene "cartridge" was isolated from pDEX011 using SmaI. The structure of the 3.2 kb cartridge is shown in FIG. 20.

5) The SmaI dextranase gene cartridge was inserted into the SmaI cloning site of pMNK, forming plasmid pMNK-1 having about 12.0 kb which was then transformed into *E. coli.*

6) Most of the transformants of *Escherichia coli* carrying pMNK-1 were characterized by an $Amp^r$, $Em^r$ phenotype and the presence of a white halo around the colony when grown on 0.2% blue dextran (Pharmacia LKB) plate.

Figure 21:
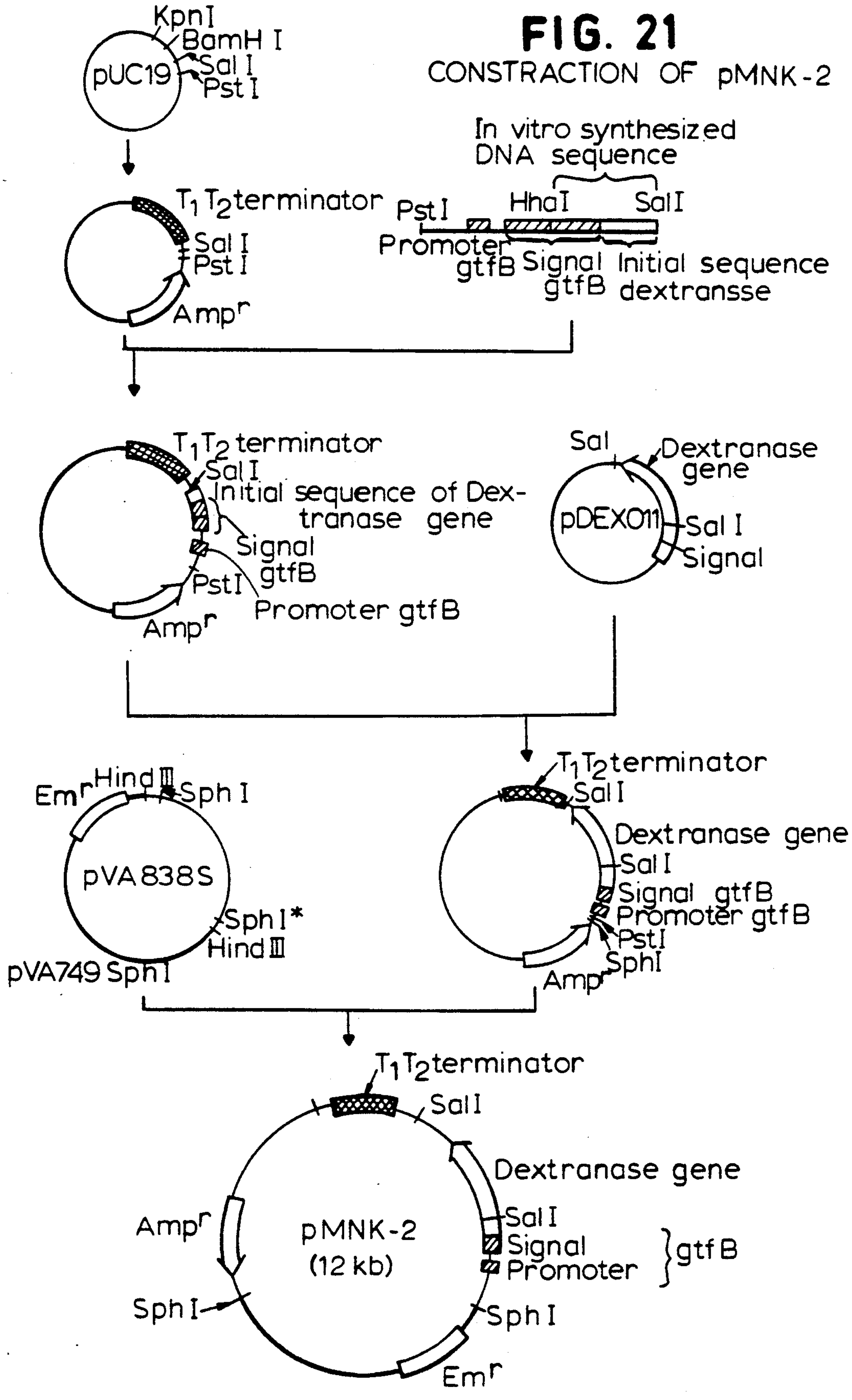
FIG. 21 is a diagramatic representation of construction of expression plasmid pMNK-2.

B. Construction of plasmid pMNK-2 (Cf. FIG. 21)

1) Plasmid pVA838 was modified to include an SphI* restriction endonuclease recognition site by insertion of a synthesized SphI adaptor adjacent the HindIII site. The resulting plasmid, pVA838S, could thus be cut with SphI restriction endonuclease to provide the $Em^r$ gene within the large fragment (designated pVA749 SphI).

2) A PstI-HhaI fragment (737bp) containing the promoter and initial signal sequence of the gtfB gene was obtained from pSU5 (Shiroza et al., supra). This was joined with an in vitro synthesized DNA . sequence (FIG. 22(b)) including the 3′ end of the signal sequence (73bp) beginning at the HhaI site and the initial 19bp of the mature dextranase sequence. The resulting composite PstI-SalI DNA fragment thus contained the promoter and signal sequence of the gtfB gene as well as the initial DNA sequence of the dextranase gene as illustrated in FIG. 22(a) and was inserted in pUC19 into which the $T_1T_2$ had already been introduced as a BamHI-SalI insert in the manner described for preparation of pMNK-1.

3) The polycloning site of the resulting plasmid was opened at the SalI site and the SalI-SalI dextranase gene fragment from pDEX011 was inserted.

4) The resulting pUC19 derivative carrying the dextranase gene with both the promoter and signal sequence of the gtfB gene was cut at the SphI site and joined with pVA749SphI. Thus, plasmid pMNK-2 (11 kb) was constructured as shown in FIG. 21.

C. Construction of plasmid pVA-pMNK pVA838 DNA was cut at NurI site and was ligated (blunt end to end) with SmaI dextranase gene cartridge mentioned above. Transformant *Escherichia coli* carrying pVA-pMNK were characterized $Em^r$, $Cm^r$ (25 μg/ml) and formation of a faint white halo around the colony when grown on on blue dextran plates.

D. Transformation of Streptococcus sanguis

It was found that *Streptococcus sanguis* strain Challis was readily transformed with plasmids pMNK-1, pMNK-2 and pVA-pMNK as $Em^r$ transformants.

As shown in Table 8, although transformants carrying pVA-pMNK cannot produce any detectable halo, transformants carrying pMNK-1 produced a faint halo after several days incubation on blue dextran plate. Detectable amount of dextranase activity were found in disrupted cellular extracts from one day liquid culture of the transformants carrying pMNK-1. This indicates that the dextranase gene on pMNK-1 is expressed and dextranase was accumulated in cytoplasm but cannot be excreted under short period-culture conditions. Transformants carrying pMNK-2 can excrete a remarkable amount of dextranase in the medium under the normal physio-logical conditions.

Preliminary Western blotting experiments show that the *Streptococcus sanguis* cell carrying pMNK-2 can produce the same mature dextranase as the original CB-8 dextranase in size but that the transformant carrying pMNK-1 produced an immature dextranase with a signal peptide.

These results indicate that the promoter from the gtfB gene is working well in *Escherichia coli* cells and *Streptococcus sanguis* cells. While the signal peptidase of *Streptococcus sanguis* recognized the cutting site of the gtfB signal peptide, that of *Escherichia coli* did not.

E. Elimination of the Insoluble Glucan Produced by *Streptococcus mutans*

To demonstrate the elimination of insoluble glucan in dental plaque, the more simple in vitro system [Takehara et al., *Archs. Oral Biol.,* 26, 217–222 (1981)] was used in place of an in vivo experiment in the oral cavity.

1) *Streptococcus mutans* was grown in the test tube containing Todd Hewitt Broth (Difco) or Brain Heart Infusion (Difco) supplemented by 2% sucrose. After standing overnight incubation at 37° C., the culture was discarded and the tube bottom was coated with white insoluble glucan at that time.

2) Each tube was again filled with Todd Hewitt Broth or Brain Heart Infusion, and was used for subsequent cultivation of *Streptococcus sanguis* harboring plasmids pVA-pMK, pMNK-1 and pMNK-2. Each different clone of *Streptococcus sanguis* was inoculated and cultivated for several hours. In some case, erythromycin (10 μg/ml) was added for the suppression of residual growth of *Streptococcus mutans.*

3) After cultivation, the culture was discarded and culture medium was replaced with an equal volume of saline. Finally, remaining insoluble glucan was sonicated and the amount of said insoluble glucan was turbidimetrically determined. As indicated in Table 9, the clone of *Streptococcus sanguis* harboring pMNK-2 eliminated insoluble glucan more effectively than the other two clones.

TABLE 8

Degree of Halo (Dextranase) Production

| harboring plasmid | Bacteria: *Escherichia coli* | Bacteria: *Streptococcus sanguis* |
|---|---|---|
| pVA-pMNK | + | − |
| pMNK-1 | +++ | + |
| pMNK-2 | +++ | ++ |

TABLE 9

Degree of Insoluble Glucan Elimination By Transformed *S. sanguis*

| harboring plasmid | None | pVA-pMNK | pMNK-1 | pMNK-2 |
|---|---|---|---|---|
| remaining insoluble glucan (%) | 100 | 98 | 90 | 6 |
| elimination efficiency (%) | 0 | 2 | 10 | 94 |

*Streptococcus mutans* microorganisms and *Streptococcus sanguis* microorganisms transformed with plasmid pMNK-2 were jointly inoculated into sterilized test tubes containing either Todd Hewitt Broth (Difco) of Brain Heart Infusion medium (Difco) containing 2% sucrose. Following shaking culture overnight at 37° C., no insoluble glucan formation was found at the bottom of the tube, signifying utility of recombinant glucanase products of the present invention in inhibiting glucan formation.

Methods have thus far been disclosed for achieving phenotypic expression of the α-1,3 glucanase II gene by cloning the gene and introducing it into bacteria indigeneous to the oral cavity.

Novel DNA sequences provided by the present invention are useful not only in securing α-1,3 glucanase II and dextranase enzyme production in heterologous host cells, but are useful as hybridization probes for isolation of α-1,3 glucanase II and dextranase enzyme encoding genes of various microbial species by well known means. In addition to the cloning of α-1,3 glucanase gene isolated from *B. circulans* BC-8 it is also possible to clone the gene coding for α-1,3 glucanase II isolated from *Pseudomonas* SK-01 (FERM P-No. 4273) and Pseudomonas (NRRL B-12324) by gene manipulation techniques similar to those disclosed above. In addition to the dextranase gene isolated from Arthrobacter sp. CB-8, it is possible to clone the gene coding for dextranase from organisms such as Coryne-bacterium AK-01 (FERM P-No. 2505), Flavobacterium BK-01-06 (FERM P-No. 1194 or FERM P-No. 1285–1288), Paecilomyces TCI-No. 9001 (FERM P-No. 6602), and *Penicillium pheniculosum* IAM-7013 (FERM P-No. 1290). Glucanase genes so isolated may then be introduced into cells of *S. sanguis* in order to promote phenotypic expression of the glucanase enzymes.

Furthermore, the combination of α-1,3 glucanase and dextranase has synergistic properties and is very effective in removing insoluble glucan. It would be possible to remove insoluble glucan most effectively by preparing a plasmid in which the α-1,3 glucanase gene and the dextranase gene are present in series downstream of a powerful promoter (e.g. gtfB gene promoter, β lactamase or streptokinase gene promoter) on a plasmid and introducing it into *S. sanguis* so as to produce the two enzymes simultaneously and secrete them effectivley. Genes encoding one or both enzymes may also be inserted into the genome of the desired host.

Bacteria other than *S. sanguis* which are indigenous to the oral cavity and might be useful in the present invention include other species of Streptococcus such as *Streptococcus salivarius*. It is possible to introduce the gene into these bacteria by methods similar to those disclosed for transforming *S. sanguis*.

What is claimed is:

1. A recombinant DNA molecule consisting of segments of DNA from different genomes which have been joined end-to-end outside of living cells and which have the capacity to transform a host and to be maintained therein, and the progeny thereof, comprising a DNA sequence selected from the group consisting of:
   (a) a DNA fragment present in Arthrobacter sp. CB-8 (FERM BP-995) and encoding α-1,6-glucan 6-glucanohydrolase,
   (b) DNA sequences which hybridize to the foregoing DNA under strigent conditions and which code on expression for α-1,6-glucan 6-glucanohydrolase, and
   (c) DNA sequences which code on expression for an α-1,6-glucan 6-glucanohydrolase enzyme of the type coded on expression by any of the forgoing DNA sequences and fragments, said DNA sequences and fragments being operatively linked to an expression control sequence in said recombinant DNA molecule.

2. A recombinant DNA molecule consisting of segments of DNA from different genomes which have been joined end-to-end outside of living cells and which have the capacity to transform a host and to be maintained therein, and the progeny thereof, comprising a DNA molecule selected from the group consisting of
   (a) a DNA fragment present in *Bacillus circulans* BC-8 (FERM BP-733) and encoding exclusively α-1,3glucan 3-glucanohydrolase,
   (b) DNA molecules which hybridize to the foregoing DNA under strigent conditions and which code on expression for exclusively α-1,3-glucan 3-glucanohydrolase, and
   (c) DNA molecules which code on expression for an α-1,3-glucan 3-glucanohydrolase enzyme of the type coded for on expression by any of the foregoing DNA molecules or fragments, said DNA molecules and fragments thereof being operatively linked to a promoter, a ribosome-binding site, and a signal in said recombinant DNA molecule.

* * * * *